(12) United States Patent
McGrath

(10) Patent No.: US 8,198,334 B2
(45) Date of Patent: Jun. 12, 2012

(54) METHODS FOR MODULATING MACROPHAGE PROLIFERATION IN OCULAR DISEASE USING POLYAMINE ANALOGS

(75) Inventor: Michael McGrath, Burlingame, CA (US)

(73) Assignee: Pathologica LLC, Burlingame, CA (US)

( * ) Notice: Subject to any disclaimer, the term of this patent is extended or adjusted under 35 U.S.C. 154(b) by 1495 days.

(21) Appl. No.: 11/064,781

(22) Filed: Feb. 22, 2005

(65) Prior Publication Data

US 2005/0256207 A1 Nov. 17, 2005

Related U.S. Application Data

(63) Continuation-in-part of application No. 09/179,383, filed on Oct. 26, 1998, now Pat. No. 7,087,648.

(60) Provisional application No. 60/063,317, filed on Oct. 27, 1997, provisional application No. 60/063,318, filed on Oct. 27, 1997.

(51) Int. Cl.
*A61K 31/13* (2006.01)
*A61K 31/655* (2006.01)
(52) U.S. Cl. ......... 514/674; 514/673; 514/151; 514/659
(58) Field of Classification Search ................... 514/674, 514/673, 151, 659
See application file for complete search history.

(56) References Cited

U.S. PATENT DOCUMENTS

| | | |
|---|---|---|
| 4,201,788 A | 5/1980 | Voorhees et al. |
| 4,847,257 A | 7/1989 | Hupe et al. |
| 5,037,846 A | 8/1991 | Saccomano et al. |
| 5,091,576 A | 2/1992 | Bergeron |
| 5,242,947 A | 9/1993 | Cherksey |
| 5,460,807 A | 10/1995 | Cardin et al. |
| 5,498,522 A | 3/1996 | Porter |
| 5,516,807 A | 5/1996 | Hupe et al. |
| 5,541,230 A | 7/1996 | Basu et al. |
| 5,580,715 A | 12/1996 | McGrath et al. |
| 5,596,011 A * | 1/1997 | Repine et al. ................. 514/369 |
| 5,639,600 A | 6/1997 | McGrath et al. |
| 5,665,588 A | 9/1997 | Kornbluth |
| 5,672,746 A | 9/1997 | Nau et al. |
| 5,677,350 A | 10/1997 | Frydman |
| 5,679,682 A | 10/1997 | Bergeron |

(Continued)

FOREIGN PATENT DOCUMENTS

EP 0162413 A2 11/1985

(Continued)

OTHER PUBLICATIONS

Hodnett et al. "Metal chelate of glyoxal and methylglyoxal," Proceedings of teh Oklahoma Acedemy of Science, 1970, vol. 49, pp. 107-111.*

(Continued)

*Primary Examiner* — Shengjun Wang
(74) *Attorney, Agent, or Firm* — Dennis A. Bennett; Suman R. Mirmira

(57) ABSTRACT

Methods for modulating macrophage proliferation in an individual afflicted with or at risk for an ocular disease such as ARMD are provided. The methods employ a polyamine analog, or salt or protected derivative thereof. Macrophage proliferation has been implicated in a number of serious disorders, including ARMD. The invention also provides methods for aiding diagnosis and monitoring therapy of an ocular disease such as ARMD.

11 Claims, 10 Drawing Sheets

U.S. PATENT DOCUMENTS

| | | | |
|---|---|---|---|
| 5,744,122 | A | 4/1998 | McGrath et al. |
| 5,820,873 | A * | 10/1998 | Choi et al. ............... 424/283.1 |
| 5,880,161 | A | 3/1999 | Basu et al. |
| 5,886,051 | A | 3/1999 | Bergeron, Jr. et al. |
| 5,889,061 | A | 3/1999 | Frydman et al. |
| 6,392,098 | B1 | 5/2002 | Frydman et al. |
| 6,537,523 | B1 | 3/2003 | McGrath et al. |
| 6,924,095 | B2 | 8/2005 | McGrath et al. |
| 7,087,648 | B1 | 8/2006 | McGrath et al. |
| 7,198,946 | B2 | 4/2007 | Marton et al. |
| 2005/0159493 | A1 | 7/2005 | McGrath et al. |
| 2005/0256207 | A1 | 11/2005 | McGrath et al. |
| 2006/0160087 | A1 | 7/2006 | McGrath et al. |
| 2007/0078187 | A1 | 4/2007 | McGrath et al. |
| 2008/0262092 | A1 | 10/2008 | Hadlock et al. |

FOREIGN PATENT DOCUMENTS

| | | | |
|---|---|---|---|
| EP | 0277635 A3 | | 8/1988 |
| EP | 0399519 A2 | | 11/1990 |
| EP | 0 415 801 A1 | | 3/1991 |
| EP | 0436632 B1 | | 7/1991 |
| JP | 60-6348 | | 2/1985 |
| JP | 08-2117670 | | 8/1996 |
| WO | WO9213548 A1 | | 8/1992 |
| WO | WO9304036 A | | 3/1993 |
| WO | WO9314782 A1 | | 8/1993 |
| WO | WO9604019 A1 | | 2/1996 |
| WO | WO 97/33175 | | 12/1997 |
| WO | WO9733175 | | 12/1997 |
| WO | WO9817624 | | 4/1998 |
| WO | WO9903823 A | | 1/1999 |
| WO | WO9921542 A2 | | 5/1999 |
| WO | WO 02/43722 | * | 6/2002 |

OTHER PUBLICATIONS

Penfold PL et al. Age-related macular degeneration: ultrastructural studies of the relationship of leucocytes to angiogenesis. Graefes Arch Clin Exp Ophthalmol 225:70-6 (1987).

Grossniklaus HE et al. Macrophage and retinal pigment epithelium expression of angiogenic cytokines in choroidal neovascularization. Mol Vis. 8:119-26 (2000).

Otani A et al. Expressions of angiopoietins and Tie2 in human choroidal neovascular membranes. Invest Ophthalmol Vis Sci. 40(9):1912-1920 (1999).

Lois N. et al. Neovascular age-related macular degeneration. Comp Ophthalmol Update 5:143-161 (2004).

Van der Schaft TL et al. Early stages of age-related macular degeneration: an immunofluorescence and electron microscopy study. Br J Ophthalmol. 77(10):657-6 (1993).

Lopez PF et al. Pathologic features of surgically excised subretinal neovascular membranes in age-related macular degeneration. Am J Ophthalmol. 112(6):647-56 (1991).

Killingsworth MC et al. Macrophages related to Bruch's membrane in age-related macular degeneration. Eye. 1990 4:613-21.

Oh H et al. The Potential angiogenic role of macrophages in the formation of choroidal neovascular membranes. Invest Ophthalmol Vis Sci. 40:1891-1898 (1999).

Tsutsumi C et al., The critical role of ocular-infiltrating macrophages in the development of choroidal neovascularization. J Leukoc Biol. 74:25-32 (2003).

Nishimura T et al. Activated macrophages in experimental subretinal neovascularization. Ophthalmologica. 200 (1):39-44 (1990).

Weller M et al. Mononuclear phagocytes in proliferative vitreoretinopathy (PVR). A specific role of microglial cells in non-traumatic disease? Eur J Ophthalmol. 1(4):161-6 (1991).

Capeans C et al. C-C chemokines in the vitreous of patients with proliferative vitreoretinopathy and proliferative diabetic retinopathy. Retina. 18(6):546-50 (1998).

Hui Y-N. et al. Prevention of experimental proliferative vitreoretinopathy with daunomycin and triamcinolone based on the time course of the disease. Graefes Arch Clin Exp Ophthalmol. 237(7):601-5 (1999).

Chen L et al. Distribution, markers, and functions of retinal microglia. Ocul Immunol Inflamm. 10(1):27-39 (2002).

Martin F et al. Proliferative vitreoretinopathy: cytologic findings in vitreous samples. Ophthalmic Res. 35(4):232-8 (2003).

Penfold PL et al. Senile macular degeneration: The involvement of immunocompetent cells. Graefes Arch Clin Exp Ophthalmol. 223:69-76 (1985).

Seddon JM et al. Association between C-reactive protein and age-related macular degeneration. JAMA 291(6):704-10 (2004).

Russell SR et al. Location, substructure, and composition of basal laminar drusen compared with drusen associated with aging and age-related macular degeneration. Am J Ophthalmol. 129(2):205-14 (2000).

Fields et al. "Fields Virology," vol. 2, 1996, Lippincott Williams & Wilkins, pp. 2418-2419.

Rizzo et al. "Pharmacokinetic profile of Mitoguazone (MGBG) in Patients with AIDS related non-Hodgkin's lymphoma," 1996, Inventigational New Drug, vol. 14, pp. 227-234.

Von Hoff, "MGBG: Teaching an old drug new tricks," 1994, Annals of Oncology, vol. 5, pp. 487-493.

Medline Abstract, AN 97070920, Rizzo et al. 1996.

Medline Abstract, AN 95001580, Von Hoff, 1995.

Basu et al.. "The ability of polyamine analogues to induce Z-DNA structure in synthetic polynucleotides in vitro inversely correlates with their effects on cytotoxicity of cis-diaminedichloroplatinum (II) (CDDP) in human brain tumor cell lines" (1996) Anticancer Res. 16:39-48.

Bellevue, III et al., "Structural comparison of alkylpolyamine analogues with potent in vitro antitumor or antiparasitic activity" (1996) Bioorg. Med. Chem. Lett. 6:2765-2770.

Bergeron et al., "Two polyamine analogs (BE-4-4-4 and BE-4-4-4-4) directly affect growth, survival, and cell cycle progression in two human brain tumor cell lines" (1995) Cancer Chemother. Pharmacol. 36:411-417.

Bitonti et al., "Bis(benzyl)polyamine analogs inhibit the growth of chloroquine-resistant human malaria parasites (Plasmodium falciparum) in vitro and in combination with .alpha.-difluoromethylornithine cure murine malaria" (1989) Proc. Natl. Acad. Sci. USA 86:651-655.

Fogel-Petrovic et al., "Effects of polyamines, polyamine analogs, and inhibitors of protein synthesis on spermidine—spermine N. sup.1-acetyltransferase gene expression" (1996) Biochemistry 35:14436-14444.

Gabrielian et al., "Effect of leukopenia on experimental post-traumatic retinal detachment" (1993) Curr. Eye. Res. 13:1-9.

Greene et al., (1991) Protective Groups in Organic Synthesis, 2nd Ed., John Wiley & Sons, Inc., New York. (Table of Contents).

Hibasami et al., "Antitumor effect of a new multienzyme inhibitor of polyamine synthetic pathway, methylglyoxal-bis (cyclopentylamidinohydrazone), against human and mouse leukemia cells" (1989) Cancer Res. 49:2065-2068.

Kramer et al., "Use of 4-fluoro-L-ornithine to monitor metabolic flux through the polyamine biosynthetic pathway" (1995) Biochem. Pharmacol. 50:1433-1443.

Marton et al., "Polyamines as targets for therapeutic intervention" (1995) Ann Rev. Pharmacol. Toxicol. 35:55-91.

McGrath et al., "Identification of a clonal form of HIV in early Kaposi's Sarcoma: Evidence for a novel model of oncogenesis, 'sequential neoplasia'" (1995) J. Acquired Imm. Def. Syn. Hum. Retro. 8:379-385.

Mukhopadhyay et al., "Effects of bis(benzyl)polyamine analogs on *Leishmania donovani* promastigotes" (1995) Exper. Parasitology 81:39-46.

Porter et al., "Polyamine inhibitors and analogues as potential anti-cancer agents" (1992) Falk Symposium 62-Polyamines in the Gastrointestinal Tract, Chapter 31, pp. 301-322.

Pulliam et al., "Unique monocyte subset in patients with AIDS dementia" (1997) Lancet 349:692-695.

Remington's Pharmaceutical Sciences, 18th edition, Mack Publishing (1990) (Table of Contents).

Shiramizu et al., "Identification of a common clonal human immunodeficiency virus integration site in human immunodeficiency virus-associated lymphomas" (1994) Cancer Res. 54:2069-2072.

Bersnstein et al. (1999). "The cellular localization of the L-orinthine decarboxylase polyamine system in normal and diseased central nervous systems," Progress in Neurobiology 57(5):485-505.

Chiang et al. (1996). "Antihuman immunodeficiency virus (HIV-1) activities of inhibitors of polyamine pathways," J. Biomed. Sci. 3(2):78-81.

Kackzmarek et al. (1992). "Inhibitors of polyamine biosynthesis block tumor necrosis factor-induced activation of macrophages," Cancer Res. 52(7):1891-1894.

Lim et al. (Mar. 14, 1995). "MGBG Therapy of relapsed extralymphatic HIV-associated non-hodgkins lymphoma (HIV NHL)," Proc. Annu. Meet. Am. Soc. Clin. Oncol. 14:A1274.

Mascolini. (1995). "Oncologists scout new directions for KS and lymphoma therapies," J. Int. Assoc. Physicians Aids Care 1(5):10-14.

Messina et al. (1992). "Polyamine involvement in functional activation of human macrophages," J. Leukoc. Biol. 52 (6):585-587.

Miles et al. (Jul. 1, 1996). "Curative therapy for AIDS cancers," Int. Conf. AIDS. XI(1):28.

Penning et al. (1998). "Sensitization of TNF-induced apoptosis with polyamine synthesis inhibitors in different human and murine tumor cell lines," Cytokine10 (6):423-431.

N.J. Prakash et al., "Antitumor Activity of Norspermidine, a Structural Homologue of the Natural Polyamine Spermidine," Anicancer Reseach 8:563-568 (1998).

M. Wojewodzka et al., "Structure-Activity Relationship of Polyamine Derivatives of 1, 3-Dichloroacetone-Thiosemicarbazone: Induction of Metastases and Increase in Sialylation of Murine Lymphoma L5178Y-R Cells," Chem. Boil. Interactions, 74 (1990) 221-23.

Ambati, et al., "An anmimal model of age-related macular degeneration in senescent Ccl-2- or Ccr-2-deficient mice." Nature Med., 2003, 9(11):1390-7.

Forrester, J.V., "Macrophages eyed in macular degeneration." Nature Med., 2003, 9(11):1350-1.

Ambati J. et al., "Age-related macular degeneration: etiology, pathogenesis, and therapeutic strategies." Surv Ophthalmol. May-Jun. 2003; 48(3):257-93.

Cousins SW et al., "Monocyte activation in patients with age-related macular degeneration: a biomarker of risk for choroidal neovascularization?" Arch Ophthalmol. Jul. 2004; 122(7):1013-8.

Cousins SW et al., "Is AMD an inflammatory disease?" Research to Prevent Blindness Library Document No. 108, www.rpbusa.org/library_content.php?document_id=108.

Hageman GS et al., "An integrated hypothesis that considers drusen as biomarkers of immune-mediated processes at the RPE-Bruch's membrane interface in aging and age-related macular degeneration." Prog Retin Eye Res. Nov. 2001; 20(6):705-32.

Haidt SJ et al., "Evidence for systemic immune activation in patients with ARMD." Print-on-Demand Abstract Book of the 2004 ARVO Annual Meeting, Feb. 23, 2004; www.arvo.org.

Penfold PL et al., "Immunological and aetiological aspects of macular degeneration." Prog Retin Eye Res. May 2001; 20(3):385-414.

Weller M. et al., "Immunochemical studies of epiretinal membranes using APAAP complexes: evidence for macrophage involvement in traumatic proliferative vitreoretinopathy" Int Ophthalmol. Jan. 1988; 11(3):181-6.

Weller M. et al., "Retinal microglia: a new cell in idiopathic proliferative vitreoretinopathy?" Exp Eye Res. Aug. 1991; 53(2):275-81.

Zarbin MA, "Current concepts in the pathogenesis of age-related macular degeneration." Arch Ophthalmol. Apr. 2004;1 22(4):598-614.

Zeiss CJ and Johnson EA, "Proliferation of microglia, but not photoreceptors, in the outer nuclear layer of the rd-1 mouse." Invest Ophthalmol Vis Sci. Mar. 2004; 45(3):971-6.

Marton, et al., Ann. Rev. Pharm. Toxicol., (1995), 35, 55-91.

Wallace, et al., Amino Acids, (2003), 26, 353-365.

Kaczmarek, et al., Cancer Res., (1992), 52, 1891-1894.

Dunzendorfer, U., et al, Some Aspects of Clearance of Mitoguazone in Cancer Patients and Experimental Cancer Models, Drug Res., (1986), 36, 506-508.

Mihich, E., Pharmacology of Methylglyoxal-bis-(guanylhydrazone) (CH3-G), Cancer Research, (1962), 22, 962-974.

Levin, Robert H., Different Patterns of Remission in Acute Myelocytic Leukemia: A Comparison of the Effects of Methyl-Glyoxal-Bix-Guanylhydrazone and 6-Mercaptopurine, Blood, (1963), 21, 6, 689-698.

* cited by examiner

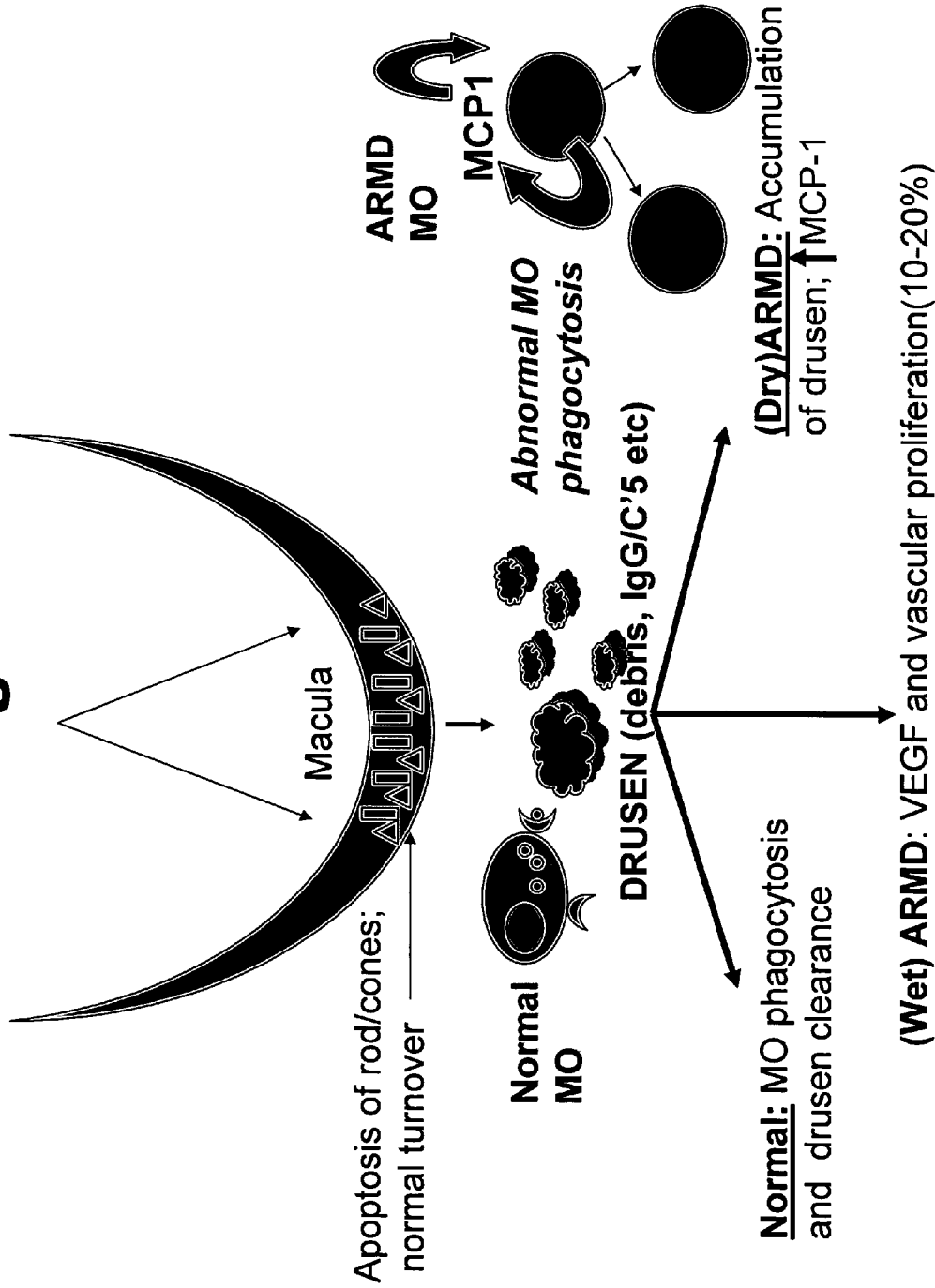

METHODS FOR MODULATING MACROPHAGE PROLIFERATION IN OCULAR DISEASE USING POLYAMINE ANALOGS

CROSS-REFERENCE TO RELATED APPLICATIONS

This application is a continuation-in-part of U.S. patent application Ser. No. 09/179,383, filed Oct. 26, 1998, which claims the benefit of U.S. Provisional Applications Ser. Nos. 60/063,317 and 60/063,318, both filed Oct. 27, 1997, all of which are incorporated by reference herein.

STATEMENT OF RIGHTS TO INVENTIONS MADE UNDER FEDERALLY SPONSORED RESEARCH

This invention was made in part during work supported by a federal grant from the National Institutes of Health, Grant No. CA 96230-03. The government may have certain rights in the invention.

TECHNICAL FIELD

This invention relates to diseases associated with proliferating macrophages, particularly as it relates to macrophage-associated ocular diseases, particularly macrophage associated retinal diseases such as vitreoretinopathy, diabetic retinopathy, and age-related macular degeneration (ARMD). More specifically, it relates to the use of polyamine analogs or salts or protected derivatives thereof to modulate macrophage proliferation, particularly in individuals afflicted with or at risk for a macrophage-associated retinal disease such as ARMD. The invention also relates to methods of aiding diagnosis, monitoring therapy, and delaying development of macrophage proliferation disorders such as ARMD that entail detection and/or modulation of macrophage proliferation.

BACKGROUND

Ocular diseases, such as degenerative cell proliferative diseases exemplified by age-related macular degeneration (ARMD), present a major health issue today. ARMD alone affects more than 1.75 million people in the U.S. It has been estimated that the number will increase to about 3 million by 2020 due to the rapid growing of the aging U.S. population. (see, e.g., Arch Ophthalmol, (2004) 122:564). ARMD is the principal cause of registered legal blindness and other visual disability among individuals over 60 years old in many parts of the world, including U.S., Western Europe, Australia, and Japan. (Ambati, et al., Surv. Ophthalmol., 48:257 May-June 2003; Zarbin, Arch. Ophthalmol., 2004, 122:598-614)

Clinical hallmarks of ARMD include drusen, hyperplasia or the retinal pigment epithelium (RPE), geographic atrophy, and choroidal neovascularization (CNV). Drusen are localized deposits of extracellular material found between the basement membrane of the RPE and Bruch's membrane. Drusen are characterized morphologically as either "soft", with fuzzy, indistinct edges, or "hard", with discrete, well-demarcated edges. Typically, drusen are clustered in the central macula, and exhibit a varied and complex morphology as determined by fundoscopic examination. It is well established in the art that the size, number and confluency of drusen are significant determinants for risk of developing ARMD. For a discussion of drusen as biomarkers of immune-mediated processes at the RPE-Bruch's membrane interface in ARMD, see Hageman et al. (2001) Retinal Eye Res. 20:705-732. In general, the precise pathogenic mechanisms that lead to ARMD are not well understood (for a review, see Zarbin, (2004), supra).

ARMD is generally characterized into two forms. The exudative or "wet" form of ARMD is characterized by CNV growth under the RPE and retina with subsequent hemorrhage, exudative retinal detachment, disciform scarring, and retinal atrophy, and can also be accompanied by serous or hemorrhagic pigment epithelial detachment. In the non-exudative or "dry" form of ARMD the accumulation of drusen is thought to cause atrophy of the macula, leading to vision loss. Wet ARMD accounts for about 75% of cases with several central vision loss. About 18% of people aged 65 to 74 years, and about 30% of people older than 74 years, have early ARMD, characterized by the presence of soft drusen or drusen with RPE degeneration or hyperpigmentation. (see, e.g., Zarbin (2004) supra)

There have been a number of reports assessing immune/inflammatory mechanisms in the formation of drusen in ARMD. One group has suggested that impaired macrophage recruitment may allow accumulation of C5a and IgG in the eye, which in turn induces vascular endothelial growth factor (VEGF) production by RPE, possibly mediating development of CNV, the primary cause of visual loss in the exudative or "wet" form of ARMD. Ambati et al. Nat Med. Nov. 9, 2003; (11):1390-7. Epub Oct. 19, 2003. Macrophages and foreign body giant calls have been reported near the Bruch's membrane where drusen is found (van der Schaft et al. Br J Ophthalmol. 1993 October; 77(10):657-61; Lopez et al. Am J Ophthalmol. 1991 112:647-56; Killlingsworth et al. Eye. 1990 4(Pt 4):613-21).

Others have hypothesized that macrophages and other inflammatory cells may be involved in CNV, which is part of the symptom in ARMD. For example, Oh et al. (Invest Ophthalmol Vis Sci 1999 40:1891-1898) suggested that IL-1β and TNF-α secreted by macrophages may promote, at least in part, angiogenesis in CNV membranes by stimulating VEGF production in RPE cells. Tsutsumi et al. (J Leukoc Biol. 2003 74:25-32) reported that mice that lack CCR2, the receptor for MCP-1, the number of infiltrating macrophage and the area of CNV were significantly reduced. Cousins et al. (Arch Ophthalmol. 2004 122:1013-8) evaluated the activation state of macrophage function in patients with age-related macular degeneration (AMD) by quantifying the production of the proinflammatory and angiogenic factor tumor necrosis factor alpha (TNF-α) and by correlating its expression with dry and wet AMD. This group reported that although wide variability in TNF-α expression by blood monocytes was observed among different patients, those patients with monocytes that expressed the greatest amount of TNF-α demonstrated higher prevalence of CNV.

Macrophages have also been reported to be associated with the Bruch's membrane in ARMD. Killingsworth, et al., Eye, 1990, 4: 613-621. Weller et al. (1991) Eur J Ophthalmol. 1:161-6 reported that posttraumatic proliferative retinopathy was apparently characterized by a severe initial inflammatory reaction as evidenced by the presence of numerous macrophages. Capeans et al. (Retina. 1998;18(6):546-50) reported that monocyte chemotactic protein-1 (MCP-1) present at significantly higher levels in the vitreous of eyes with vitreoretinal disorders than the vitreous of control eyes, and hypothesized that MCP-1 may be involved in the recruitment of macrophages and monocytes into the vitreous of eyes with proliferative vitreoretinal disorders. Other groups have reported that macrophages are activated in rabbits during the inflammatory phase of the development of proliferative vitreoretinopathy (PVR). Hui et al. Graefes Arch Clin Exp Ophthalmol. 1999 July, 237(7): 601-5; Chen et al. Ocul Immunol Inflamm. Mar. 10, 2002 (1): 27-39; Martin et al. Ophthalmic Res. 2003 July-August, 35(4): 232-8.

Other immune mechanisms have also been implicated in ARMD. For example, auto-antibodies with specificity for retinal tissue have been detected in ocular pathologies, including ARMD (Penfold et al. Graefes Arch Clin Exp Ophthalmol. 1985 223:69-76). C-reactive protein, a serum protein associated with inflammation, is elevated in subjects with ARMD. (Seddon et al. (2004) JAMA 291:704-10) At the tissue level, confirmation of inflammatory cell infiltrates has been documented for early, intermediate, and late stage disease. (Penfold et al. (1985) Graefes Arch Clin Exp Ophthalmol. 223:69-76) Immunohistochemical analysis of drusen has demonstrated the presence of immunologic antigens, to include complement components C5, C5b-9, immunoglobulin, and HLA-DR. (Russell et al. (2000) Am J Ophthalmol. 129:205-14) For a review of the immunological and etiological aspects of macular degeneration, see Penfold et al. (2001) Retinal Eye Res 20:382-414.

More recently, the role of macrophages in ARMD has been examined using transgenic mice deficient for either monocyte chemoattractant protein (MCP-1), or its cognate chemokine receptor, CCR-2. (Ambati et al. (2003) Nat Med. 9:1390-7). These transgenic animals developed ARMD abnormalities that include the characteristic display of RPE drusen, accumulation of lipofuscin, photoreceptor atrophy, and CNV. Ambati et al. hypothesized that impaired macrophage recruitment may allow accumulation of C5a and IgG, which induces vascular endothelial growth factor (VEGF) production by RPE, possibly mediating development of CNV.

Diagnosis and prognosis of ARMD has primarily focused on assessing drusen (e.g., total drusen area or the size of drusen), which has been identified as the most important conventional risk factors for ARMD progression (Latkany (2004) medscape.com/viewarticle/494566). Other conventional techniques in screening and diagnosis include fluorescence angiography (FA), optical coherence tomography (OCT), spectral OCT, and scanning laser ophthalmoscope with OCT (SLO-OCT). Therapies for ARMD are largely in the experimental stage and focus on treatment of wet ARMD. Exemplary therapies include those directed toward inhibition of neovascularization such as laser photocoagulation, photodynamic therapy (which may be accompanied by administration of a light-activated drug such as VISUDYNE®), transpupillary thermotherapy, microcurrent stimulation, and administration of antiangiogenic agents, radiation therapy, and surgery. A review of convention therapies is provided by Lois et al. (2004) Comp Ophthalmol Update 5:143-161.

There is a need for methods of indicating development and/or progression of these ocular diseases such as ARMD, and for treatment of such diseases. The present invention addresses these needs.

Additional Literature
Ocular Diseases, Including ARMD

Additional literature which may be of interest relating to ocular diseases, and particularly ARMD, includes: Penfold et al. (1987) Graefes Arch Clin Exp Ophthalmol 225:70-6; Killingsworth et al. (1990) Eye 4:613-621; Nishimura et al. (1990) Ophthalmologica 200:39-44; Weller et al. (1991) Exp Eye Res. 53(2):275-81); Otani et al. (1999) Invest Ophthalmol Vis Sci 40:1912-1920; Grossniklaus et al. (2000) Mol Vis 8:119-26; Spandau et al. (2000) Invest Ophthalmol Vis Sci 41:S836; Van der Schaft et al. (2001) Invest Ophthalmol Vis Sci 33:3493; Grossiklaus et al. (2002) Mol. Vis 8:119-226.

Macrophayes

Macrophages are terminally differentiated cells generally incapable of further cell division. Macrophage proliferation has been implicated in certain serious proliferative diseases such as lymphoma, cardiovascular disease, and nephrosclerosis. U.S. Pat. No. 5,639,600. Gabrielian et al. reported the role of macrophage infiltration in traumatic proliferative vitreoretinopathy. ((1994) Curr. Eye. Res. 13: 1-9). McGrath et al. disclosed the involvement of clonally expanded macrophages in the induction of cancerous tumor growth and AIDS dementia. U.S. Pat. Nos. 5,639,600 and 5,580,715; see also Pulliam et al. (1997) Lancet 349:692-695; McGrath et al. (1995) J. Acquired Imm. Def Syn. Hum. Retro. 8: 379-385; Shiramizu et al. (1994) Cancer Res. 54:2069-2072.

Polyamine Analogs and Anti-proliferative Activity

Certain anionic oligomers have antiproliferative activity. In particular water soluble polyureas and polyamides with a molecular weight of less than 10,000 inhibit smooth muscle cell proliferation in culture and in vivo, and have been suggested for treatment of atherosclerosis (U.S. Pat. No. 5,460, 807; see also U.S. Pat. No. 5,516,807 (relating to use of bis-ethyl norspermine in vascular proliferative disorders)). Certain triazoles are antiproliferatives; in particular amino 1, 2, 3 triazoles inhibit labeled thymidine incorporation into intact pig skin, inhibit keratinocyte proliferation, and have been suggested for use in treatment of psoriasis, a chronic skin disease characterized by epidermal hyperproliferation (U.S. Pat. No. 4,847,257). Derivatives of valproic acid decrease neuro-2a cell proliferation in vitro, and have been suggested for use in prevention and treatment of neurodegenerative disorders such as Alzheimer's disease to inhibit pathologic neural cell growth (U.S. Pat. No. 5,672,746).

The level of polyamines is intimately related to cell proliferation. Cellular levels of polyamines are carefully regulated by opposing synthetic and catabolic pathways. Compounds that are able to lower polyamine levels are proposed for use in the treatment of rapidly proliferating host cells such as cancer and psoriasis. A key polyamine catabolizing enzyme spermidine-spermine N1-acetyltransferase (SSAT) is among the few genes known to be inducible by the natural polyamines. Certain polyamine analogs exaggerate this response. 1,11-diethylnorspermine (DENSPM) increases SSAT mRNA levels in human melanoma cells up to 20-fold, with an increase in immunodetectable SSAT protein by 300-fold. By comparison, natural polyamine spermine is far less effective, increasing SSAT mRNA by ~3-fold and immunodetectable protein by ~7-fold. Fogel-Petrovic et al.(1996) Biochemistry 35:14435. Polyamine analogs also induce Z-DNA structure in vitro. This property correlates inversely with the effects on cis-diaminedichloroplatinum (II) (CDDP) cytotoxicity in human brain tumor cells. Basu et al. (1996) Anticancer Res. 16:39.

U.S. Pat. No. 5,498,522 outlines the use of SSAT, or other determinants related to SSAT induction such as SSAT cofactor acetylCoA, and the SSAT products N1-acetylspermine and N1-acetylspermidine, as a prognostic indicator or tumor response marker. Measurement of these determinants is proposed as a prognostic indicia and tumor response marker to evaluate the clinical effectiveness of anticancer agents comprising polyamine analogs. Hibasami et al. [(1989) Cancer Res. 49:2065] prepared methylglyoxal-bis(cyclopentylamidinohydrazone) (MGBCP) as an inhibitor of the natural polyamine synthetic pathway. MGBCP inhibits S-adenosylmethionine decarboxylase, spermine synthase, and spermine synthetase, competing with S-adenosylmethionine, spermidine, and putrescine, respectively. MGBCP depleted spermidine and spermine in leukemic ascites cells, and prolonged survival time of mice bearing P388 leukemia.

U.S. Pat. No. 5,541,230 (Basu et al.) indicates that spermine derivatives decrease growth in a number of human tumor cell lines, and propose their use in cancer chemotherapy. Bergeron et al. (*Cancer Chemother. Pharmacol.*) showed that the polyamine analogs 1,14-bis(ethylamino)-5, 10-diazatetradecaone (BE-4-4-4), and 1,19-bis(ethylamino)-5,10,15-triazanonadecane (BE-4-4-4-4; see U.S. Pat. No. 5,541,230)) directly affects growth, survival, and cell cycle progression in human brain tumor cell lines. For other publications relating to the synthesis and use of certain polyamines, the reader is referred to EP 277,635, EP 162,413, EP 399,519, JP 85/6348, and U.S. Pat. No. 5,679,682; and to Bellevue et al. (1996) *Bioorg. Med. Chem. Lett.* 6:2765, and Porter et al. (1992) *Falk Symposium* 62:201; Marton and Pegg (1995) *Ann Rev. Pharmacol. Toxicol.* 35:55-91.

SUMMARY OF THE INVENTION

The present invention provides methods for modulating proliferating macrophages using a composition comprising a polyamine analog or salt or protected derivative thereof, preferably in an individual afflicted with or at risk for a disease with which macrophage proliferation is associated, particularly a macrophage-associated ocular disease, more particularly a macrophage-associated retinopathy, wherein the composition is administered in amount sufficient to modulate proliferating macrophages in the individual.

In another aspect, the invention features a method for increasing phagocytic activity of macrophages in an individual having or at risk of a macrophage-associated ocular disease (e.g., a macrophage-associated retinal disease (particularly macrophage-associated retinopathy, e.g., macrophage-associated retinal disease, e.g., ARMD, particularly dry ARMD) by administering to the individual a composition comprising a compound selected from a polyamine analog, a salt of a polyamine analog, and a protected derivative of a polyamine analog, in an amount sufficient to enhance macrophage phagocytosis in the individual; wherein said administering provides for an increase in phagocytic activity of macrophages in the individual (e.g., an increase in phagocytic activity of a population containing macrophages, e.g., blood macrophages, e.g., as found in a population of peripheral blood monocytes) in the individual).

In one aspect of the invention, the invention provides a method of aiding diagnosis of a macrophage-associated ocular disease (e.g., a macrophage-associated retinal disease (particularly macrophage-associated retinopathy, e.g., macrophage-associated retinal disease, e.g., ARMD, particularly dry ARMD) in an individual by detecting in a biological sample for the individual the level of proliferating macrophages (e.g., by assessing a level of cells having markers of proliferating macrophages, e.g., CD14+/CD16+ cells, CD16+/PCNA+ cells) and/or by assessing a level of systemic MCP-1. An elevated level of proliferating macrophages, or elevated level of systemic MCP-1, relative to a normal level of proliferating macrophages or systemic MCP-1 (i.e., a level of such markers in an non-diseased, preferably age-matched control) indicates an increased risk of, or the presence of, a macrophage-associated ocular disease. In a related embodiment, sensitivity of proliferating macrophages to a polyamine analog is tested, which sensitivity is indicative of the presence of a macrophage-associated disease. Where an increased risk of a macrophage-associated ocular disease, such as ARMD, is identified using such a diagnostic test, the patient can be identified for diet modification, increased frequency of follow-up visits to a clinician, and more frequent tests to assess progression toward disease.

In a further aspect of the invention, the invention provides a method of monitoring therapy of a macrophage-associated ocular disease (e.g., a macrophage-associated retinal disease) in an individual comprising detecting the level of proliferating macrophages (and/or a level of systemic MCP-1) in a biological sample from said individual.

In another aspect of the invention, the invention provides a method of modulating macrophage proliferation in an individual afflicted with or at risk for a macrophage-associated ocular disease (e.g., a macrophage-associated retinal disease, more particularly a vitreoretinopathy, with the "dry" form of ARMD being of particular interest) comprising administering to the individual a composition comprising a compound selected from the group consisting of a polyamine analog, a salt of a polyamine analog, and a protected derivative of a polyamine analog, wherein all nitrogen atoms of said polyamine analog are secondary, tertiary, or quarternary amino groups, and where the composition is administered in an amount sufficient to modulate macrophage proliferation in the individual.

In another aspect of the invention, the invention provides a method of decreasing a level or accumulation of drusen in a subject comprising administering to the individual a composition comprising a compound selected from the group consisting of a polyamine analog, a salt of a polyamine analog, and a protected derivative of a polyamine analog, wherein all nitrogen atoms of said polyamine analog are secondary, tertiary, or quarternary amino groups, and where the composition is administered in an amount sufficient to modulate macrophage proliferation in the individual.

In one aspect of the invention, the invention provides a method of delaying development of a macrophage-associated ocular disease (e.g., a macrophage-associated retinal disease, more particularly a vitreoretinopathy, with the "dry" form of ARMD being of particular interest) in an individual comprising administering to the individual an effective amount of an agent that modulates macrophage proliferation. In a related embodiment, delaying development is assessed by stabilization of, reduction of, drusen (e.g., as assessed by drusen score).

These and other features as well as advantages of the invention will be readily apparent to the ordinarily skilled artisan upon reading the instant specification.

BRIEF DESCRIPTION OF THE DRAWINGS

FIG. 4C is a schematic showing a hypothesis of the disease mechanism underlying ARMD pathogenesis. (MO=macrophage)

DETAILED DESCRIPTION OF THE INVENTION

Figure 1:
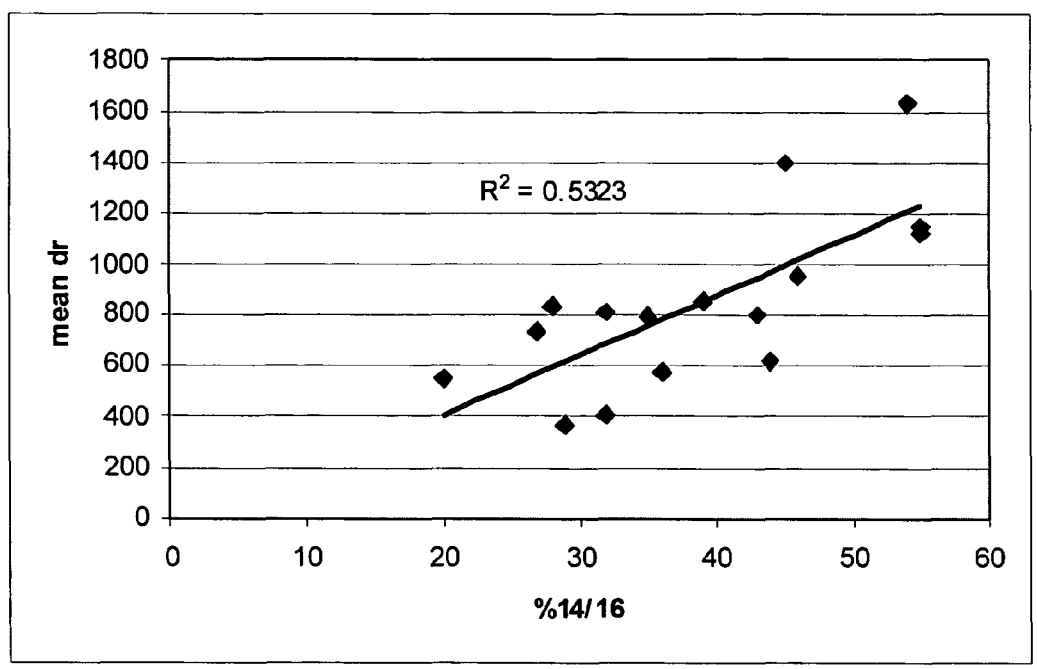
FIG. 1 is a graph showing the relationship between blood macrophage (CD14/16+) and immune activation (mean HLA-DR level) in ARMD patient samples. It shows that the higher the level of macrophages in the blood (% CD14+/16+) the higher the level of activation (higher HLA-DR expression/cell) in ARMD patient blood.

The invention is based on the discovery that polyamine analogs are particularly effective in modulating macrophage proliferation. Further, the invention is based on the discovery that certain proliferative diseases are associated with, and may be supported by, proliferation macrophages. Among these cellular proliferative diseases are ocular diseases, particularly retinopathies such as vitreoretinopathy, age-related macular degeneration (ARMD), and the like. The invention is further based on the discovery that polyamine analogs can be used in the treatment of non-exudate or "dry" ARMD. In addition, the invention is based on the discovery that systemic MCP-1, as well as markers of macrophage activation (e.g., CCR2 expression levels, CD14/CD16 expression levels, CD14/PCNA expression levels) are indicative of ARMD disease severity, based on their correlation with drusen, the conventional ARMD disease severity marker.

For example, it was discovered ARMD patients have elevated, abnormal levels of macrophage proliferation in peripheral blood. In addition, the level of activated macrophages in blood parallels the level of drusen formation in the retina of both wet and dry ARMD patients. Without wishing to be bound by a particular theory, macrophage proliferation is associated with, and may contribute to, ocular diseases, particularly retinal diseases such as ARMD (including wet and dry ARMD), proliferative vitreoretinopathy (PVR), and proliferative diabetic retinopathy (PDR).

The invention is further based on the observation that the level of activated macrophages in the peripheral blood of patients parallels the level of cellular activation of the macrophages. In addition, the invention is based on the discovery that the polyamine analog SL-11047 can kill activated macrophage cells isolated from ARMD patients. Controlling unwanted and harmful macrophage proliferation and activation is thus a crucial aspect of developing new, effective treatment modalities for macrophage-associated disorders, including these macrophage-associated ocular diseases.

Accordingly, the invention provides methods for modulating macrophage proliferation, which are useful for controlling, palliating, and/or delaying development of macrophage-associated diseases, with macrophage-associated ocular diseases, particularly macrophage-associated retinal diseases (including, but not limited to, ARMD, vitreoretinopathy, and diabetic retinopathy) being of particular interest. The invention also provides methods of modulating macrophage proliferation in individuals afflicted with or at risk for a macrophage-associated ocular disease, particularly a macrophage-associated ocular disease such as ARMD. The invention also provides methods of aiding diagnosis and/or monitoring therapy of such diseases which entail measuring the presence of proliferating macrophages.

As discussed below, exemplary agents for modulation of macrophages are polyamine analogs especially 1,11-bis(ethyl)norspermine; 1,8-bis(ethyl)spermidine (BES); 1,12-bis(ethyl)spermine (BESm; DESPM (N1, N12-diethylspermine); 1,11-bis(ethylamino)-4,8-diazaundecane (BE-3-3-3); 1,14-bis(ethylamino)-5,10-diazatetradecane (BE-4-4-4) (Diethylhomospermine, N1, N14-diethylhomospermine; DEHOP or DEHSPM); diethyl-norspermine (DENOP); 1,19-bis(ethylamino)-5,10,15-triazanonadecane (BE-4-4-4-4); N-ethyl-N'-(2-(3'-ethylamino-propylamino methyl)-cis-cyclopropylmethyl)-propane 1,3-diamine tetrahydrochloride (SL-11037); N-ethyl-N'-(2-(3'-ethylamino-propylamino methyl)-trans-cyclobutylmethyl)-propane 1,3-diamine tetrahydrochloride (SL-11038); N-ethyl-N'-(2-(3'-ethylamino-propylamino methyl)-trans-cyclopropylmethyl)-propane 1,3-diamine tetrahydrochloride (SL-11044; and N,N'-bis(3-ethylaminopropyl)-cis-but-2-ene-1,4-diamine tetrahydrochloride (SL-11047).

Definitions

As used herein, the terms "macrophage" and "monocyte" are used interchangeably, as it is understood that in the art the term "monocyte" is often used to describe a circulating mononuclear cell that expresses the CD14 cell surface marker, and when in a tissue this cell is also classified as a macrophage.

A "proliferating macrophage" is a term understood in the art and as used herein denotes a macrophage which is dividing. Normally a macrophage is a terminally differentiated cell incapable of further division. For purposes of this invention, a "proliferating macrophage" is capable of further division or is in a portion of the cell cycle not considered to be terminal or end stage. Preferably, the proliferation is clonal, i.e., is derived from a single cell. Methods of detecting proliferating macrophage(s) is discussed below.

As used herein, detecting the "presence of proliferating macrophages" generally means detecting the level of proliferating macrophages. It is understood that an absolute or even relative level need not be determined; an observation of detectable proliferating macrophages is sufficient.

An "ocular disease" refers to a disease, disorder, or abnormality that relates to the state of the eye, particularly the ability of the eye to perceive images. "Ocular disease" encompasses retinal diseases, including proliferative diseases of the eye. Exemplary ocular diseases include ARMD (including exudative ("wet") and non-exudative ("dry")), vitreoretinopathy, diabetic retinopathy, and the like. The terms "disorder" and "disease" are used interchangeably herein.

"Proliferative retinopathy" as used herein refers to an ocular disease involving growth, displacement, hypertrophy or hyperplasia of cellular or acellular components of the retina and/or vitreous including, where such components include vascular cells; blood vessels; glial cells; fibrocytes; macrophages; inflammatory cells; retinal pigment epithelial cells; astrocytes or sensory retinal cells including photoreceptors (rods and cones); bipolar cells; and ganglion cells. Drusen are products of proliferative retinopathy, as drusen can be regarded as growths in Bruch's membrane, which is an acellular layer beneath retinal pigment epithelial cells. Further, drusen can cause displacement of retinal pigment epithelial cells, and may also facilitate hyperplasia, hypertrophy or hypotrophy of retinal pigment epithelial cells. "Proliferative retinopathy" includes, but is not necessarily limited to, ARMD (both wet and dry), proliferative diabetic retinopathy (PDR), traumatic prolifertative retinopathy, and proliferative vitreoretinopathy (PVR).

A "macrophage-associated" disease, disorder or indication is a disease, disorder or indication that is associated with an elevated, or abnormal, level of macrophage proliferation as compared to control sample(s). Such disorders include, but are not limited to, ocular diseases having a proliferating macrophage component (e.g., retinal disease (e.g., ARMD, vitreoretinopathy, diabetic retinopathy, and the like)). Macrophage-associated retinopathies are of particular interest. Macrophage-associated ocular disease can generally be characterized as having a high frequency of activated macrophages in tissues compared to a frequency of such cells in non-disease controls, where activated macrophages can be identified by CD16 expression, elevated HLA-DR, elevated MCP-1 production, decreased CCR2 expression, and elevated PCNA (relative non-disease macrophages).

An individual "afflicted with" an ocular disease (e.g., a retinal disease (e.g., ARMD, vitreoretinopathy, and the like) means that the individual has been diagnosed as having, or is suspected as having, an ocular diseases such as ARMD, vitreoretinopathy, and diabetic retinopathy, etc.

By a "polyamine", a term well-understood in the art, is meant any of a group of aliphatic, straight-chain amines derived biosynthetically from amino acids; polyamines are reviewed in Marton et al. (1995) Ann. Rev. Pharm. Toxicol. 35:55-91. By "polyamine" is generally meant a naturally-occurring polyamine or natural polyamine, which are naturally produced in eukaryotic cells. Examples of polyamines include putrescine, spermidine, spermine and cadaverine.

By "polyamine analog" is meant an organic cation which shares structure with, but is non-identical to, naturally-occurring polyamines such as spermine and/or spermidine and their precursor, diamine putrescine. Polyamine analogs can be branched or un-branched, or incorporate cyclic moieties. Examples of polyamine analogs include, without limitation, N1, N14-diethylhomo-spermine (DEHSPM) and N1, N12-diethylspermine (DESPM). See, for example, WO 98/17624 and U.S. Pat. No. 5,541,230. U.S. Pat. Nos. 5,037,846 and 5,242,947 disclose polyamines comprising primary amino groups. Especially preferred are polyamine analogs wherein all nitrogen atoms of said polyamine analogs are independently secondary, tertiary, or quartenary amino groups.

An "alkyl" is a cyclic, branched, or straight chain chemical group containing carbon and hydrogen, such as methyl, butyl, t-butyl, pentyl, cyclopropyl, and octyl. Alkyl groups can be either unsubstituted or substituted with one or more substituents, e.g., halogen, alkoxy, acyloxy, amino, hydroxyl, mercapto, carboxy, benzyl. Alkyl groups can be saturated or unsaturated (e.g., containing —C=C— or —C°C— subunits), at one or several positions. Unless otherwise specified, alkyl groups will comprise 1 to 8 carbon atoms, preferably 1 to 6, and more preferably 1 to 4 carbon atoms. "Cycloalkyl" refers to cyclic alkyl groups only, such as cyclopropyl, cyclobutyl, cyclopentyl, etc. "n-alkyl" refers to a linear (i.e., straight-chain) alkyl group only, while "branched alkyl" refers to branched alkyl groups to the exclusion of cyclic and linear alkyl groups. "Alkenyl" refers to a cyclic, branched, or straight chain chemical group containing carbon and hydrogen where at least one bond is monounsaturated, such as ethenyl, cyclopentenyl, or 1,3-butadienyl. Alkenyl groups can be substituted as indicated for alkyl groups. Alkenyl groups can be designated as cyclic, linear (n-alkenyl) or branched in an analogous fashion to the preceding designations for alkyl. An "aryl" is an unsaturated aromatic carbocyclic group having a single ring (e.g., phenyl), or multiple condensed rings (e.g., naphthyl), which can optionally be unsubstituted or substituted with amino, hydroxyl, alkyl, alkoxy, chloro, halo, mercapto and other substituents.

A "stereoisomer" is defined as any optical isomer of a compound, including enantiomers and diastereomers. Unless otherwise indicated, structural formula of compounds are intended to embrace all possible stereoisomers.

A "salt" is defined as a compound formed by the replacement of one or more hydrogen atoms with elements or groups, which is composed of anions and cations, which usually ionizes in water; a salt is formed, for instance, by neutralization of an acid by a base. A polyamine analog salt can comprise, for example, chloride ions.

"Protected derivative" is used to refer to a compound protected with a protecting group. "Protecting group" refers to a chemical group that exhibits the following characteristics: 1) reacts selectively with the desired functionality in good yield (preferably at least 80%, more preferably at least 90%, more preferably at least 95%, still more preferably at least 99%) to give a protected substrate that is stable to the projected reactions for which protection is desired; 2) is selectively removable from the protected substrate to yield the desired functionality; and 3) is removable in good yield (preferably at least 80%, more preferably at least 90%, more preferably at least 95%, still more preferably at least 99%) by reagents compatible with the other functional group(s) present or generated in such projected reactions. Examples of suitable protecting groups can be found in Greene et al. (1991) Protective Groups in Organic Synthesis, 2nd Ed. (John Wiley & Sons, Inc., New York). Exemplary protecting groups for the amino functionality include, but are not limited to, mesitylenesulfonyl (MesSO$_2$), benzyloxycarbonyl (CBz), t-butyloxycarbonyl (Boc), t-butyldimethylsilyl (TBDIMS), 9-fluorenylmethyloxycarbonyl (Fmoc), or suitable photolabile protecting groups such as 6-nitroveratryloxy carbonyl (Nvoc).

An "individual" is a vertebrate, preferably a mammal, more preferably a human. Mammals include, but are not limited to, farm animals, sport animals, rodents, primates, and pets. A "non-HIV-infected individual" is an individual who has not been infected by HIV. An "HIV-infected" individual may or may not yet display clinical manifestations of infection. HIV and methods of detecting HIV infection are well known in the art and need not be discussed herein.

As used herein, "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples. Generally, the sample will be, or be derived from, peripheral blood. Preferably, the blood will have been enriched for a macrophage fraction, by using, for example, glass or plastic adherence. As used herein, reference to a "blood sample" is meant to encompass whole blood as well as fractions derived from whole blood, with samples containing immune cells, particuarly peripheral blood monocytes, being of particular interest. Other biological samples of interest include, but are not limited to, ocular samples obtained from eye tissue or fluids, e.g., vitreal fluid, aqueous fluid, and retinal or choroid biopsies.

As used herein, the term "biomarker" refers to a molecule (e.g., protein, nucleic acid, or chemical compound (e.g., substrate, metabolite, catabolite, and the like), whether large or small, which, when present in a biological sample of an individual, is indicative of the presence of a particular physiological trait in the individual. For example, PCNA is biomarker for the presence of proliferating macrophages in a biological sample. In another example of biomarker, the molecule Monocyte Chemoattractant Protein MCP-1 is a biomarker for the presence of activated macrophages.

As used herein, "aiding diagnosis" means that these methods assist in making a clinical determination regarding the classification, or nature, of the ocular disease, and may or may not be conclusive with respect to the definitive diagnosis. The method of aiding diagnosis of an ocular disease, particularly a retinal disease, can comprise the step of detecting the level of proliferating macrophages in a biological sample from the individual and determining whether the proliferating macrophage level is abnormal (e.g., elevated) relative to a level associated with an unaffected individual. In general, abnormal levels of proliferating macrophages can indicate the individual is susceptible or sensitive to development of a proliferative retinopathy, particularly ARMD, PVR, or PDR. Determining whether an ocular disease (e.g.,. retinal disease) may or may not be associated with proliferating macrophages, particularly clonal macrophage proliferation, and making this classification can assist in developing and recommending treatment strategies as well as evaluating prognosis. For example, where an individual has increased proliferating macrophages further diagnostic tests (e.g., OCT, FA, and the like) may be indicated, and/or frequency of follow-up visits.

"Development" of an ocular disease, such as a retinal disease, herein means initial manifestations and/or ensuing progression of the disease. Development of disease can be detectable and assessed using any suitable standard clinical techniques, such as visual observation of the size of drusen, the presence of bleeding in the diseased eye, the structure of the retina, loss or degradation of vision or the visual field, and the like. Clinical signs and symptoms for various ocular diseases, including retinopathies, are well known in the art. As used herein, development also refers to disease progression that may be undetectable by use of conventional signs and symptoms. For purposes of this invention, progression refers to the biological course of the disease state. "Development" includes occurrence, recurrence, and onset. As used herein "onset" or "occurrence" of a neurological disorder includes initial onset and/or recurrence. As used herein, "delaying" development of disease means to defer, hinder, slow, retard, stabilize, and/or postpone development of the disease. This delay can be of varying lengths of time, depending on the history of the disorder and/or the medical profile of the individual being treated. As is evident to one skilled in the art, a sufficient or significant delay can, in effect, encompass prevention, in that the individual does not develop detectable disease. A method that "delays" development of disease is a method that reduces the extent of the disease in a given time frame, when compared to not using the method. Such comparisons are typically based on clinical studies, using a statistically significant number of subjects, although this knowledge can be based upon anecdotal evidence. "Delaying development" can mean that the extent and/or undesirable clinical manifestations are lessened and/or time course of the progression is slowed or lengthened, as compared to not administering the agent. Thus the term also includes, but is not limited to, alleviation of symptoms, diminishment of extent of disease, stabilized (i.e., not worsening) state of disease, delay or slowing of disease progression, and remission (whether partial or total) whether detectable or undetectable.

As used herein, an "effective amount" (e.g., of an agent) is an amount (of the agent) that produces a desired and/or beneficial result. An effective amount can be administered in one or more administrations. For purposes of this invention, an effective amount is an amount sufficient to produce modulation of macrophage proliferation. An "amount (of a polyamine analog) sufficient to modulate macrophage proliferation" preferably is able to alter the rate of proliferation of macrophages by at least 25%, preferably at least 50%, more preferably at least 75%, and even more preferably at least 90%.

Such modulation may have desirable concomitant effects, such as to palliate, ameliorate, stabilize, reverse, slow or delay progression of disease, delay or even prevent onset of disease.

As used herein, the term "agent" means a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic compounds based on various core structures, and these are also included in the term "agent". In addition, various natural sources can provide compounds, such as plant or animal extracts, and the like. Agents include, but are not limited to, polyamine analogs. Agents can be administered alone or in various combinations.

"Modulating" proliferating macrophages as used means a change in a level of proliferating macrophages of at least 25%, preferably at least 50%, more preferably at least 75%, and even more preferably at least 90%. A decrease in proliferating macrophages can result from, for example, a decrease that results following administration of an agent, such as a polyamine analog, that interferes with natural polyamine interaction with DNA (including, but not limited to, interfering with a polyamine biosynthetic pathway, interfering with the intracellular concentration of spermidine, competitors, inhibitors of DNA interaction by a natural polyamine, interfering with polyamine metabolism, etc.). Generally, for purposes of this invention, "modulating" a level of proliferating macrophages means that the qualitative or quantitative level of proliferating macrophages (e.g., as detected using a biomarker such as PCNA), and further which may be expressed as a portion of total macrophages (e.g., percent CD16+/CD14+ or percent PCNA-CD14 positive compared to total CD14 positive) is decreased when compared to the level in that individual when no agent is administered.

A "target" of a polyamine or polyamine analog is an entity which interacts, either directly or indirectly, with the polyamine or polyamine analog(s). Examples of targets are DNA, RNA, and/or membranes.

Methods of the Invention

The invention contemplates both methods of treatment (e.g., using polyamine analogs, and other agents that inhibit macrophage proliferation and/or disrupt a polyamine biosynthetic pathway) which methods have as a therapeutic endpoint modulation of proliferation macrophages (e.g., a decrease in proliferating macrophages (e.g., a decrease in the percentage of PBMCs that are proliferating macrophages) and/or a decrease in a rate of proliferation of such macrophages). The invention also contemplates methods of diagnosis of a macrophage-associated ocular disease, particularly a macrophage-associated retinal disease, by assessing particular biomarkers that are indicators of proliferating macrophages. These methods are described in more detail below.

Methods of Modulating Proliferating Macrophages

The invention provides methods for modulating proliferating macrophages in an individual afflicted with or at risk for a macrophage-associated ocular disease, particularly a macrophage-associated retinal disease, comprising administering a polyamine analog, a salt of a polyamine analog, or a protected derivative of a polyamine analog, in an amount sufficient to modulate macrophage proliferation in the individual (i.e., an effective amount). Alternatively, a composition comprising a polyamine analog, or a protected derivative of a polyamine analog is administered in an amount sufficient to modulate proliferating macrophages (i.e., an effective amount). Examples of macrophage-associated ocular diseases have been described above, and include, but are not limited to, macrophage-associated retinal diseases. Exemplary diseases of interest includes, but are not limited to, ARMD (wet and dry), vitreoretinopathy, and diabetic retinopathy. Treatment of vitreoretinopathy and dry ARMD are of particular interest. Polyamine analogs are discussed below.

The invention further provides methods for decreasing drusen, or preventing further accumulation of drusen, in a in an individual afflicted with or at risk for a macrophage-associated ocular disease, particularly a macrophage-associated retinal disease, comprising administering a polyamine analog, a salt of a polyamine analog, or a protected derivative of a polyamine analog, in an amount sufficient to modulate macrophage proliferation in the individual (i.e., an effective amount). Alternatively, a composition comprising a polyamine analog, or a protected derivative of a polyamine analog is administered in an amount sufficient to modulate proliferating macrophages (i.e., an effective amount). Reducing drusen, or at least preventing further accumulation of drusen, can provide for prevention or a delay in development of a macrophage-associated ocular disease. Drusen can be assessed according to conventional techniques, and therapy can be assessed by reduction of drusen score, or maintenance of a drusen score (e.g., a drusen score indicative of early ARMD of 1-2). Of particular interest is maintenance of a drusen score that is indicative of less severe disease according to conventional criteria.

For purposes of this invention, an individual suitable for administration of a polyamine analog (or an agent which modulates macrophage proliferation) is one who has been diagnosed as or suspected of having an ocular disease, particularly a retinal disorder such as ARMD, vitreoretinopathy, or diabetic retinopathy, or who is adjudged to be at high risk for developing such a disorder. As is evident to one skilled in the art, these methods can apply to those individuals not displaying any symptoms. An "at risk" or "high risk" individual is an individual who has a discrete and significant risk of developing an ocular disease, particularly a retinal disease. An "at risk" or "high risk" individual may or may not have detectable disease, and may or may not have displayed detectable disease prior to receiving the method(s) described herein. "High risk" (or "at risk") denotes that an individual has one or more so-called risk factors, which are measurable parameters that correlate with development of disease. An individual having one or more of these risk factors has a higher probability of developing disease than an individual without these risk factor(s). These risk factors include, but are not limited to, drusen score, genetic (i.e., hereditary) considerations (including family history and genetic markers), and presence or absence of appropriate chemical markers and exposure to environments, conditions, or factors which would increase the possibility of acquiring a particular disease. Retroviral infections, especially retroviral insertions into particular genetic loci (such as fur or PDGF), may also be considered a risk factor. A high risk individual has one, preferably two, more preferably three, risk factors. However, it is understood that having only one risk factor can often indicate high risk.

Despite the advances in research and development in the area of ocular diseases, such as retinal diseases, only certain risk factors have been found so far to play a role in the disease development. Such factors can be aging, gender, genetic, nutrition or stress-related. Because all risk factors for developing an ocular disease are not known, and the interplay among these factors (in terms of overall risk) are not fully understood, it is clear to one skilled in the art that individuals suitable for administration of an agent for purposes of this invention can have clinical features in common, and that individuals not falling clearly in the categories described above can nonetheless be considered suitable candidates for administration of an agent. For example, an individual who has a family history of ARMD could be considered at risk for developing ARMD herself, even though no obvious symptom has been observed. In this context, administration of an agent to such an individual could result in delay of occurrence of disease, even to the extent that the individual does not develop ARMD within his or her lifetime (or develops it later than would have been expected). Another example is an individual who is being treated using other modes of therapy, and who is showing clinical responsiveness to the therapy (i.e., stabilization or remission). Such an individual may be adjudged as at "high risk" even though the initial course of therapy is not yet completed, due to projection of clinical progress by the clinician, and can be a suitable candidate for receiving an agent before completion of the initial therapy. The clinician, as one skilled in the art, has discretion to determine whether treatment using an agent may be indicated.

In another embodiment, the invention provides methods for modulating macrophage proliferation in an individual (who is generally afflicted with or at risk of for a macrophage associated disease) comprising administering a composition comprising an effective amount of an agent that interferes with polyamine interaction with proliferating macrophage target, such as DNA, RNA, and/or membranes. An agent that interferes with polyamine interaction with a proliferating macrophage target(s) is one which interferes with any aspect of natural polyamine synthesis and/or metabolism, intracellular concentration regulation, and/or function (i.e., interaction with DNA).

Diagnostic Methods and Kits

The present invention further provides methods for aiding in the diagnosis of an individual having or at risk of having, or monitoring therapy in individuals having, a macrophage-associated ocular disease, particularly a retinal disease such as ARMD, vitreoretinopathy, and diabetic retinopathy.

In one embodiment, these methods involve detecting the presence of proliferating macrophages in a biological sample from the individual, e.g., by detecting a biomarker of a proliferating macrophage (e.g., CD14+/CD16+ cells or CD14+/PCNA+ cells, e.g., as a percentage of peripheral blood monocytes (PBMCs)), where the presence of a level of proliferating macrophages present in the sample that is significantly greater than a level of a non-disease control is an indicator of risk or the presence of a macrophage-associated ocular disease. In another embodiment, the diagnostic methods involve detecting a level of CCR2 expression in PBMCs, where a decreased level of CCR2 expression relative to a level found in non-diseased controls is indicative of proliferating macrophages, which in turn is an indicator of risk or the presence of a macrophage-associated ocular disease. In still another embodiment, the diagnostic methods involve detecting systemic MCP-1 levels (levels of MCP-1 in the peripheral blood, i.e., other than in the eye per se), where systemic MCP-1 levels elevated relative to a systemic MCP-1 level in a non-disease control is indicative of proliferating macrophages in the individual, which in turn is an indicator of risk or the presence of a macrophage-associated ocular disease. Throughout, reference to an elevated (or decreased) level relative to a non-disease control is generally meant to encompass a different that is at least 1 standard deviation above (or below) an average value for normal, age-matched non-disease controls.

In those individuals considered at high or significant risk of developing ARMD or other ocular disease, detection of proliferating macrophages, CCR2 levels (e.g., as expressed on the surface of monocytes), and/or MCP-1 levels in a biological sample (e.g., a biological sample containing peripheral blood monocytes (PBMCs) may also assist in alerting the individual and/or the clinician of possible precursor disease. Thus, the invention also includes methods of monitoring an individual at risk or high risk of developing a macrophage-associated ocular disease, particularly a macrophage-associated retinal disease, comprising detection of proliferating macrophages, CCR2 levels, and/or MCP-1 levels in a biological sample from that individual (e.g., in a blood sample, e.g., a blood sample containing PBMCs). In one embodiment, the individual is "afflicted with" (e.g., diagnosed as having, suffering from and/or displaying one or more clinical symptoms of) a particular disease, disorder or indication, or at "risk" for (e.g., having a genetic predisposition for, or family history of, or being environmentally exposed to factors which increase the probability of acquiring) a particular disease, disorder, or indication.

In another embodiment, the invention provides methods of monitoring therapy of an ocular disease, particularly a retinal disease, comprising detecting the presence of (e.g., the level of) proliferating macrophages, CCR2 levels (e.g., as expressed on the surface of monocytes), and/or MCP-1 levels in a biological sample. As the level of macrophage proliferation is associated with these conditions, monitoring these levels may in turn indicate initial responsiveness and efficacy, as well as the appropriate dosage of the therapy. It is understood that monitoring therapy or an individual at (high) risk means that biological sample(s) are obtained at different times, for example, during application of therapy, and are compared, either with each other, a control, and/or a desired value. In one embodiment, monitoring therapy includes the step of detecting macrophage proliferation.

Detection of proliferating macrophage(s), macrophage markers (e.g., CD14, CD16, PCNA, HLA-DR, CCR2, and the like) and MCP-1 levels can be achieved using any of several techniques. In some embodiments of the invention involving detection of macrophage proliferation, proliferation is measured in relation to circulating macrophages, and is performed on a leukocyte preparation from peripheral blood. In other embodiments of the invention, proliferation is measured in relation to tissue-fixed macrophages, typically performed on tissue sections.

Proliferating macrophages may be detected, for example, by assaying cell proliferative markers, such as PCNA. These markers are distinct from those that identify only "activated" macrophages (as opposed to proliferating macrophages), such as CD69 and CD25. The cellular subset representing macrophages may be identified by detection of certain cell specific markers, such as CD14, CD68, CD16, or nonspecific esterase. Detection of these cell-type and/or proliferative markers use methods standard in the art, such as staining techniques and FACS sorting and analysis. These methods are further described in Example 1. Further, it is possible that these proliferating macrophages could be distinguished based on other characteristics, such as cell density (as measured in PERCOLL™ gradients, for example). These determinations may be established empirically using standard techniques in the art.

Methods for assessing CCR2 levels can be performed according to methods known in the art. In one embodiment a CCR2 expression level is determined by contacting an anti-CCR2 antibody with a blood sample, usually a blood-derived sample, containing peripheral blood monocytes.

Methods for assessing MCP-1 levels are also well known in the art for example, MCP-1 can be detected using an anti-MCP-1 antibody in an ELISA using a blood sample, usually a blood-derived sample, containing peripheral blood monocytes.

For the purpose of aiding in the diagnosis of or predicting an ocular disease, particularly a retinal disease, the level of proliferating macrophages, CCR2 expression, and/or MCP-1 in a sample is generally compared with a mean or median level in samples taken from healthy individuals, matched where necessary for sex and age. A level of proliferating macrophages, or a level of CCR2 expressing cells, can be calculated as the absolute number of proliferating macrophages or CCR2+ cells obtained from a blood sample (or detected by immunohistopathology of a tissue section). More usually, the level is calculated as a percentage of total macrophages in the sample, identifiable by cell markers or morphological characteristics, since this normalizes for differences in the number of macrophage-like cells recovered in the sample. Similarly, MCP-1 levels in a biological sample can be determined either quantitatively or qualitatively and compared to an MCP-1 level associated with unaffected (healthy) individuals.

As with many clinical tests, a finding of greater than about two, usually at least about three, standard deviations above the average associated with a normal (non-diseased, preferably age-matched) value is statistically significant and indicates an abnormality. A finding of about one or about two standard deviations, above the average is reason for concern, although, as described herein, can be an indicator of a less severe form of disease (e.g., a disease severity associated with a drusen score of 1-2, rather than a relative increased disease severity associated with a drusen score of 3-4). In combination with other indicators, an elevated level of a marker of a macrophage-associated ocular disease as described herein can aid in diagnosis of, for example, ARMD, or some other condition associated with macrophage proliferation. In general, markers of macrophage activation, as well as systemic MCP-1 production, can serve as markers of a macrophage-associated ocular disease, with levels of such markers serving as markers of disease severity.

For example, peripheral blood leukocytes stained and counted for PCNA/CD14 or CD16/CD14 cells are indicative of the presence of proliferating macrophages, which in turn is consistent with macrophage-associated ocular disease, particularly a macrophage-associated retinal disease, in the level of such cells is elevated relative to a non-disease, age-matched control. In addition, a level of proliferating macrophages is also indicative of the severity of a macrophage-associated ocular disease in the subject, with higher levels of proliferating macrophages (e.g., a greater percentage of proliferating macrophages of total PBMCs) being associated with increased disease severity (e.g., a higher drusen score).

In another example, a decreased level of peripheral blood leukocytes stained and counted for CCR2 expression compared to healthy individuals is consistent with a macrophage-associated ocular disease in the individual if the percentage of positively stained cells is significantly less than that of a percentage of CCR2+ cells from a non-disease, age-matched control. Decreased CCR2 expression levels are also indicative of the severity of a macrophage-associated ocular disease in the subject, with lower levels of CCR2 expression (e.g., CCR2-expressing cells as a percentage of total PBMCs, or a mean CCR2 expression level of total PBMCs) being associated with increased disease severity (e.g., a higher drusen score).

In another example, a decreased level of peripheral blood leukocytes stained and counted for intensity of HLA-DR expression on macrophages compared to healthy individuals is consistent with a macrophage-associated ocular disease in the individual if the percentage of positively stained macrophages is significantly greater than that level found in a non-disease, age-matched control. The higher the intensity of HLA-DR staining, the greater the severity of disease. Elevated HLA-DR expression levels are also indicative of the severity of a macrophage-associated ocular disease in the subject, with higher levels of HLA-DR expression (e.g., HLA-DR-expressing macrophages as a percentage of total PBMCs or macrophages, or a mean HLA-DR expression level of total PBMCs) being associated with increased disease severity (e.g., a higher drusen score).

In another example, an elevated level of MCP-1 in blood of a subject (systemic MCP-1, as opposed to MCP-1 levels in the eye or eye tissue per se) compared to a non-disease, age-matched control is consistent with a macrophage-associated ocular disease in the individual if the MCP-1 levels are significantly greater than a systemic MCP-1 level of non-disease, age-matched controls. MCP-1 levels are also indicative of the severity of a macrophage-associated ocular disease in the subject, with higher MCP-1 levels being associated with increased disease severity (e.g., a higher drusen score).

In another example, sensitivity of MCP-1 production and/or macrophages from an individual to a polyamine analog can also be indicative of a macrophage-associated ocular disease in the individual. A decrease of MCP-1 production by such macrophages, or inhibition of growth of such macrophages, in the presence of a polyamine analog (e.g., in culture) is another indicator that the individual from whom the macrophages were obtained has or is at risk of a macrophage-associated ocular disease. A decrease in MCP-1 production of at least 25%, 50%, 75%, 85% or more, or effective growth inhibition (including killing) of at least 25%, 50%, 75%, 85% or more of macrophages in a sample, in the presence of a polyamine analog as compared to MCP-1 production or cell growth in the absence of the polyamine analog is indicative of sensitivity of the macrophage to the polyamine analog.

The differential diagnosis will include any condition associated with macrophage proliferation as a causative or consequential effect, with the ultimate diagnosis being the responsibility of the managing physician or clinician, and can be assessed in the context of other clinical signs or symptoms, if present.

For the purpose of monitoring the effect of a macrophage proliferation inhibitor, the level of proliferating macrophages in a treated sample is generally compared with the level in an untreated sample. For the general screening of proliferation inhibitors, peripheral blood leukocytes are isolated from an individual affected with a disease associated with proliferating macrophages. Samples of the cells are treated with the candidate compound, and the effect is compared with cells not treated. When administered to a patient, the effect of a macrophage proliferation inhibitor is determined by comparing the level of proliferating macrophages before and during treatment, with a downward trend generally being consistent with a positive effect.

In another embodiment, the invention provides methods of delaying development of a macrophage-associated ocular disease, particularly a macrophage-associated retinal disease. These methods comprise administration of an effective amount of an agent which modulates macrophage proliferation to the individual. Such agents, which include polyamine analogs (including stereoisomers, their salts, and protected derivatives thereof), are described below. The invention also includes methods of treatment or palliation of these disorders using an agent(s) which modulates macrophage proliferation.

Kits

The invention also provides kits using in the diagnostic methods of the invention. In general the kits include detection means for detecting one or more biomarkers for a macrophage-associated ocular disease, particularly macrophage-associated retinal disease, in a biological sample, usually a blood sample, from a subject. Such biomarkers include biomarkers for proliferating macrophages (e.g., PCNA, and the like as discussed herein), activated macrophage (e.g., CD14, CD16, PCNA, CCR2, HLA-DR ("dr")), and MCP-1.

Agents For Modulating Macrophage Proliferation

In some embodiments of the invention, macrophage proliferation is accomplished by using a polyamine analog (including stereoisomers, salts, and protected derivatives thereof). In other embodiments, any agent which modulates macrophage proliferation may be used. With respect to polyamine analogs, it is understood that the discussion also applies to stereoisomers, salts and protected derivatives thereof.

Polyamine Analogs

The polyamine analogs used in the present invention include compounds of the structures 1, 2, 3, 4, and 5, and the corresponding stereoisomers, salts, and protected derivatives thereof:

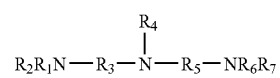

1 where $R_1$, $R_2$, $R_4$, $R_6$ and $R_7$ are independently selected from the group consisting of hydrogen, alkyl and aryl, and where $R_3$ and $R_5$ are alkyl groups;

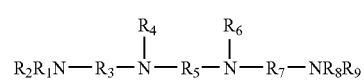

2 where $R_1$, $R_2$, $R_4$, $R_6$, $R_8$, and $R_9$ are independently selected from the group consisting of hydrogen, alkyl and aryl, and where $R_3$, $R_5$ and $R_7$ are alkyl groups;

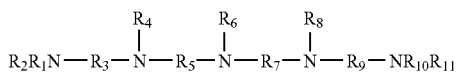

where $R_1$, $R_2$, $R_4$, $R_6$, $R_8$, $R_{10}$ and $R_{11}$ are independently selected from the group consisting of hydrogen, alkyl and aryl, and where $R_3$, $R_5$, $R_7$ and $R_9$ are alkyl groups;

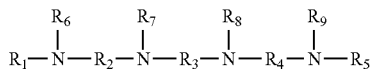

where $R_1$ and $R_5$ are independently selected from the group consisting of methyl, ethyl, n-propyl, and isopropyl;

where $R_2$, $R_3$, and $R_4$ are independently selected from the group consisting of $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ alkyl-$C_3$-$C_{10}$ aryl-$C_1$-$C_6$ alkyl;

and where $R_6$, $R_7$, $R_8$ and $R_9$ are independently selected from the group consisting of H, methyl, and ethyl;

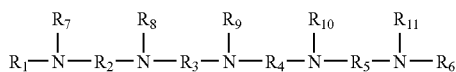

where $R_1$ and $R_6$ are independently selected from the group consisting of methyl, ethyl, n-propyl, and isopropyl;

where $R_2$, $R_3$, $R_4$ and $R_5$ are independently selected from the group consisting of $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ alkyl-$C_3$-$C_{10}$ aryl-$C_1$-$C_6$ alkyl;

and where $R_7$, $R_8$, $R_9$, $R_{10}$ and $R_{11}$ are independently selected from the group consisting of H, methyl, and ethyl.

Preferably, the polyamine analogs will include compounds of the structures 2 and 3, where $R_3$, $R_5$, $R_7$ and $R_9$ are independently $(CH_2)_x$ groups, where x is an integer from 2 to 6, and further where $R_4$, $R_6$ and R8 are hydrogen atoms.

More preferably, the polyamine analogs will include compounds of the structures 2 and 3, where R3, R5, R7 and R9 are independently (CH2)x groups, where x is an integer from 2 to 6, and where R4, R6 and R8 are hydrogen atoms, and where R1 and R10 are alkyl groups, and further where R2 and R11 are hydrogen atoms.

Most preferably, the polyamine analogs will include compounds of the structures 2 and 3, where R3, R5, R7 and R9 are independently $(CH_2)_x$ groups, where x is an integer from 2 to 6, and where $R_4$, $R_6$ and $R_8$ are hydrogen atoms, and where $R_1$ and $R_{10}$ are alkyl groups, and where $R_2$ and $R_{11}$ are hydrogen atoms, and further where the polyamine analogs have a molecular weight less than 500.

Additional preferred compounds also include compounds of the structure 4,
where $R_6$, $R_7$, $R_8$ and $R_9$ are H;
where $R_1$ and $R_5$ are ethyl;
where $R_6$, $R_7$, $R_8$ and $R_9$ are H and $R_1$ and $R_5$ are ethyl;
and/or where $R_2$ and $R_4$ are independently selected from the group consisting of $C_1$-$C_6$ alkyl and $R_3$ is selected from the group consisting of $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ alkyl-$C_3$-$C_{10}$ aryl-$C_1$-$C_6$ alkyl.

Additional polyamine analogs useful in the present invention include compounds of the formula 6, and the corresponding stereoisomers, salts, and protected derivatives thereof:

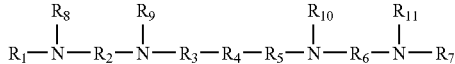

where $R_4$ is $C_2$-$C_6$ n-alkenyl, $C_3$-$C_6$ cycloalkyl, $C_3$-$C_6$ cycloalkenyl, or $C_3$-$C_6$ aryl; $R_3$ and $R_5$ are independently chosen from a single bond, $C_1$-$C_6$ alkyl, or $C_1$-$C_6$ alkenyl;

$R_2$ and $R_6$ are independently chosen from $C_1$-$C_6$ alkyl, $C_1$-$C_6$ alkenyl, $C_3$-$C_6$ cycloalkyl, $C_3$-$C_6$ cycloalkenyl, or $C_3$-$C_6$ aryl;

$R_1$ and $R_7$ are independently chosen from H, $C_1$-$C_6$ alkyl, or $C_2$-$C_6$ alkenyl; and $R_8$, $R_9$, $R_{10}$, and $R_{11}$ are H.

In preferred embodiments of the compounds of formula 6, $R_1$ and $R_7$ are independently chosen from $C_1$-$C_6$ alkyl or $C_2$-$C_6$ alkenyl.

Additional polyamine analogs useful in the present invention include compounds of the formula 7, and the corresponding stereoisomers, salts, and protected derivatives thereof:

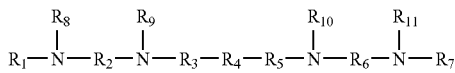

where $R_4$ is $C_1$-$C_6$ n-alkyl or $C_1$-$C_6$ branched alkyl;
$R_3$ and $R_5$ are independently chosen from a single bond or $C_1$-$C_6$ alkyl;

$R_2$ and $R_6$ are independently chosen from $C_1$-$C_6$ alkyl, $C_1$-$C_6$ alkenyl, $C_3$-$C_6$ cycloalkyl, $C_3$-$C_6$ cycloalkenyl, or $C_3$-$C_6$ aryl;

$R_1$ and $R_7$ are independently chosen from H, $C_1$-$C_6$ alkyl, or $C_2$-$C_6$ alkenyl; and $R_8$, $R_9$, $R_{10}$, and $R_{11}$ are H.

In preferred embodiments of the compounds of formula 7, $R_1$ and $R_7$ are independently chosen from $C_1$-$C_6$ alkyl or $C_2$-$C_6$ alkenyl, $R_4$ is $C_1$-$C_6$ saturated n-alkyl or $C_1$-$C_6$ saturated branched alkyl, and $R_3$ and $R_5$ are independently chosen from a single bond or $C_1$-$C_6$ saturated n-alkyl.

When compounds of formulas 1-7 contain terminal primary amino groups (that is, in compounds of formula 1, when $R_1$ and $R_2$ are both H, and/or $R_6$ and $R_7$ are both H; in compounds of formula 2, when $R_1$ and $R_2$ are both H, and/or $R_8$ and $R_9$ are both H; in compounds of formula 3, when $R_1$ and $R_2$ are both H, and/or $R_{10}$ and $R_{11}$ are both H; in compounds of formula 4, when $R_1$ and $R_6$ are both H, and/or $R_5$ and $R_9$ are both H; in compounds of formula 5, when $R_1$ and $R_7$ are both H, and/or $R_6$ and $R_{11}$ are both H; in compounds of formula 6, when $R_1$ and $R_8$ are both H, and/or $R_7$ and $R_{11}$ are both H; in compounds of formula 7, when $R_1$ and $R_8$ are both H, and/or $R_7$ and $R_{11}$ are both H), the diseases treated with such compounds include all diseases disclosed herein except Alzheimer's disease.

Preferably, all the nitrogens of the polyamine analog are independently secondary, tertiary, or quarternary amino groups.

Among polyamine analogs preferred for use in this invention are those compounds with a demonstrated ability to modulate naturally occurring polyamine levels in cells. Without intending to be limited by theory, possible mechanisms include competition in the polyamine synthesis pathway; upregulation of polyamine catabolizers such as SSAT; affecting polyamine metabolism.

Of special interest are the following polyamine analogs:
1,11-bis(ethyl)norspermine (1,11-bis(ethylamino)-4,8-diazaundecane; BE-3-3-3)
1,8-bis(ethyl)spermidine (BES)
1,12-bis(ethyl)spermine (BESm; DESPM ($N^1$, $N^{12}$-diethylspermine; SunPharm);
1,14-bis(ethylamino)-5,10-diazatetradecane (BE-4-4-4) (Diethylhomospermine, $N^1$, $N^{14}$-diethylhomospermine; DEHOP or DEHSPM; SunPharm)
diethyl-norspermine (DENOP; SunPharm)
1,19-bis(ethylamino)-5,10,15-triazanonadecane (BE-4-4-4-4)
N-ethyl-N'-(2-(3'-ethylamino-propylamino methyl)-cis-cyclopropylmethyl)-propane 1,3-diamine tetrahydrochloride (SL-11037), provided by S'LIL, Madison, Wis.
N-ethyl-N'-(2-(3'-ethylamino-propylamino methyl)-trans-cyclobutylmethyl)-propane 1,3-diamine tetrahydrochloride (SL-11038), S'LIL
N-ethyl-N'-(2-(3'-ethylamino-propylamino methyl)-trans-cyclopropylmethyl)-propane 1,3-diamine tetrahydrochloride (SL-11044), S'LIL.
N,N'-bis(3-ethylaminopropyl)-cis-but-2-ene-1,4-diamine tetrahydrochloride (SL-11047), S'LIL
The structures of SL-11037, SL-11038, SL-11044, and SL-11047 are diagrammed below:

such as macrophage-associated ocular diseases, particularly macrophage-associated retinal diseases).

Any polyamine analog listed above, or stereoisomers, salts or protected derivatives thereof (or a composition comprising an effective amount of any polyamine analog listed above, or stereoisomers, salts or protected derivatives thereof) may be used in vitro or in vivo. In vitro, a suitable biological sample (such as a blood sample, which may or may not be enriched for the macrophage population) is contacted with the composition(s). In vivo, a composition of the invention is generally administered according to the manufacturer's/supplier's instructions. Generally, polyamine analogs are administered by subcutaneous or intravenous injection. They may also be administered orally.

In vivo Administration

The amount of a polyamine analog (or stereoisomers, salts or protected derivatives thereof) administered will depend on several variables, such as the particular analog (or sterioisomer, salt or protective derivative) used, the time course of administration, the condition of the individual, the desired objective, the extent of disease, how many doses will be administered, and whether any other substances are being administered. Generally, the amount used will be as recommended by the manufacturer and/or based on empirical studies. In the case of polyamine analogs (or stereoisomer, salt, or protected derivative thereof), the amount will generally be between about 1 to about 300 mg/m$^2$/day, possibly between about 15 to about 150 mg/m$^2$/day. Administration is generally

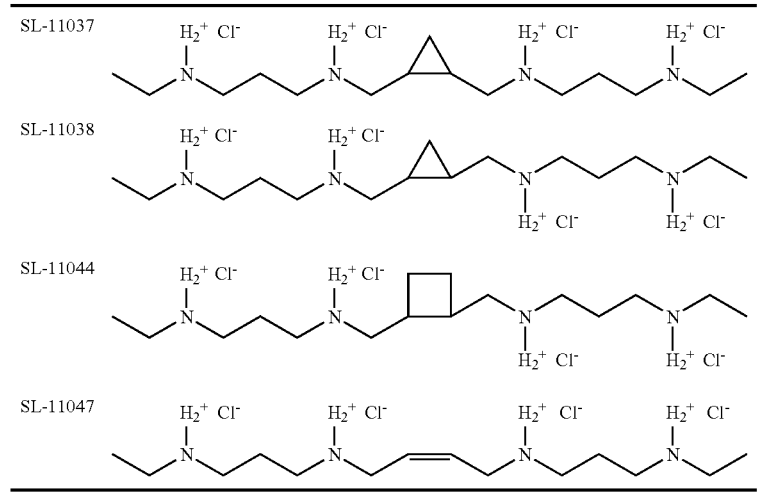

Besides the polyamine analogs listed above, stereoisomers, salts or protected derivatives thereof, may be used.

Methods of Use of Polyamine Analogs

The invention also comprises methods of using an effective amount of any of the polyamine analogs listed above, or stereoisomers, salts or protected derivatives thereof (or a composition comprising an effective amount of any of the polyamine analogs listed above, or stereoisomers, salts or protected derivatives thereof) in modulating macrophage proliferation (or in treating or delaying development of macrophage-associated diseases, such as macrophage-associated ocular diseases, particularly macrophage-associated retinal diseases). The invention also comprises any polyamine analog listed above, or stereoisomers, salts or protected derivatives thereof, for use in preparing compositions (i.e., medicaments) useful for treating macrophage-associated diseases, intermittant, meaning that analog (or stereoisomer, salt, or protected derivative thereof) is administered per a period of at least one to two days and then not administered for a period of at least one to two days, with the cycle repeated as indicated. In one embodiment, the polyamine analog (or stereoisomer, salt, or derivative thereof) for 6 days every three weeks.

Routes of administration will generally depend on the nature of the particular polyamine analog (or stereoisomer, salt or protective derivative) used, and may be, for example, oral or by injection (intraocular (e.g., intravitreal), subcutaneous or intravenous). Other routes of administration include topical administration (to the eye, e.g., using eye drops), subconjunctival, periocular, subtenon, retrobublar (retro-orbital), or by iontophoretic delivery to the eye.

Formulations

Preferably, a polyamine analog (or stereoisomer, salt or protected derivative), or other suitable agent that interferes with the polyamine synthetic pathway, polyamine metabolism, and/or the intracellular concentration maintenance of spermine) is administered in a suitable pharmaceutical excipient. Pharmaceutical excipients are known in the art and are set forth in *Remington's' Pharmaceutical Sciences,* 18th edition, Mack Publishing (1990).

The polyamine analog may also be associated with another substance that facilitates agent delivery to macrophages, or increases specificity of the agent to macrophages. For example, an agent(s) may be associated into liposomes. Liposomes are known in the art. The liposomes in turn may be conjugated with targeting substance(s), such as IgGFc receptors. Substances that increase macrophage phagocytosis such as zymosan or tetrachlorodecaoxygen (TCDO) and/or activation such as MCSF, GMCSF or IL-3 may be used to increase uptake of anti-proliferative agent(s). In one embodiment, the polyamine analog is provided as a sustained release formulation which can be placed, for example, in the eye or adjacent a vascular bed that leads to the eye.

A polyamine analog (or stereoisomer, salt or protected derivative) may be administered alone, or in conjunction with other substances and/or therapies, depending on the context of administration (i.e., desired end result, condition of the individual, and indications). "In conjunction with" means that an agent is administered prior to, concurrently, or after other substance or therapy. Examples of substances that might be administered in conjunction with an agent include, but are not limited to, antibiotics (e.g., agents to treat or prevent bacterial, viral or fungal infection), anti-inflammatory agents, anti-angiogenic agents, and the like. For example, a polyamine analog (or a stereoisomer, salt or protected derivative thereof) can be administered in conjunction with mitoguazone dihydrochloride.

The mechanistic effectiveness of various polyamine analogs and enzyme inhibitors can be determined at least in part by their ability to deplete intracellular polyamine pools. Kramer et al. [(1995) *Biochem. Pharmacol.* 50:1433] describe the use of 4-fluoro-L-ornithine to monitor metabolic flux through the polyamine biosynthetic pathway. It was determined that the metabolic flux indicated by the rate of appearance of fluorinated polyamines, reflected the proliferation status of the cells. U.S. Pat. No. 5,498,522 outlines the use of SSAT as a prognostic indicator or tumor response marker. Either SSAT enzyme activity, SSAT enzyme protein, or mRNA transcripts can be measured directly, or other determinants related to SSAT induction can be measured, such as SSAT co-factor acetylCoA, and the SSAT products N1-acetylspermine and N1-acetylspermidine. To further determine the effect of a polyamine analog's administration, an individual may be monitored for disease (or precursor disease) progression as well as biochemical and/or genetic markers of disease (or precursor disease). With respect to disease progression, multiple rating scales (i.e., indices of clinical function) have been established and are known in the art for various macrophage proliferative disorders such as AD and lymphomas. For macrophage-associated neurological disorders, cognitive functions can be tested and, in some cases, imaging modalities such as MRI may be used.

Other Agents for Modulating Macrophage Proliferation

Besides the polyamine analogs described above, suitable agents for use in modulating macrophages in the context of macrophage-associated ocular diseases, particularly macrophage-associated retinal diseases, include general anti-proliferative agents (i.e., proliferation-modulating agents), which agents inhibit proliferation of macrophages. These include, but are not limited to, daunomycin, mitomycin C, daunrorubicin, doxorubicin, 5-FU, cytocine arabinoside, colchicine, cytochalasin B, bleomycin, vincristin, vinblastine, methotrexate, cis platinum, ricin, abrin, diphtheria toxin, and saporin.

Other suitable agents would be those which inhibit, or interfere with, the polyamine synthetic pathway, or those which affect the metabolism of polyamines. Other suitable agents are those which affect the closely regulated intracellular concentration of spermidine. An example of such an agent is MGBG (mitoguazone dihydrochloride; XYRKAMINE®; Ilex, Tex.) which inhibits S-adenosylmethionine decarboxylase which in turn is required for the production of polyamines. Any agent that interferes with polyamine interactions with proliferating macrophage target, such as DNA, RNA, and/or membranes would likewise be suitable. Another type of useful agent is one that interferes with polyamine interactions with DNA. Such an agent(s) could exert this function, for example, by any of the effects above (i.e., interfering with the polyamine synthetic pathway and/or metabolism, disturbing the concentration of intracellular spermine, competitors, etc.) as well as affecting polyamine function in terms of interacting with DNA. It is understood that, with respect to these and any other agent described herein, toxicology considerations also must be taken into account when determining whether, and/or in what amount, an agent is to be used.

Administration and other considerations have been described above. Contents of all references and publications cited herein are hereby incorporated in their entirety.

The following examples are provided to illustrate but not to limit the invention.

EXAMPLES

Example 1

Immune Cell Activiation in Wet and Dry ARMD

The purpose of this example was to determine levels of immune activation on peripheral blood monocytes and T-cells in subjects with ARMD. Further, the purpose was to determine whether levels of peripheral activation were correlated with clinically determined levels of drusen progression. Immune cell activation markers of choice included HLA-DR, CD16 (FC gamma III), and CD38.

Methods and Materials:

Subjects. The study included 32 subjects with ARMD (9 dry, 23 wet), and from 10 age-matched control subjects. Macular drusen were graded from 1 to 4 on basis of size, number, soft vs. hard & associated pigment abnormalities. The grades of macular drusen were not disclosed to the laboratory assessing macrophage abnormalities. Fundus photographs (see Results) illustrate the different grades. Table I provides the drusen scores in the right and left eyes of each of the ARMD subjects in the study. Unless specifically indicated, all subsequent data for ARMD patients uses average drusen values from both wet and dry ARMD patients.

TABLE I

| ARMD Cohort | | | |
|---|---|---|---|
| subject | Age | Drusen score right eye | Drusen score left eye |
| 1 | 84 | 4 | 4 |
| 2 | 88 | end stage FV scar | 4 |
| 3 | 83 | 4 | 4 |
| 4 | 83 | end stage FV scar | 3 |
| 5 | 84 | end stage FV scar | 4 |

TABLE I-continued

ARMD Cohort

| subject | Age | Drusen score right eye | Drusen score left eye |
|---|---|---|---|
| 6 | 87 | scar | 1 |
| 7 | 87 | 2 | end stage scar |
| 8 | 82 | end stage FV scar | 2 |
| 9 | 73 | 1 | 1 |
| 10 | 85 | end stage FV scar | 4 |
| 11 | 84 | 3 | 3 |
| 12 | 78 | 4 | 4 |
| 13 | 80 | 2 | 2 |
| 14 | 90 | 3 | 3 |
| 15 | 77 | end stage FV scar | end stage FV scar |
| 16 | | 2 | 2 |
| 17 | | end stage FV scar | 5 |
| 18 | 82 | 1 | SRN, 1 |
| 19 | 84 | 4 | 4 |
| 20 | 77 | | |
| 21 | 66 | SRN | 1 |

TABLE I-continued

ARMD Cohort

| subject | Age | Drusen score right eye | Drusen score left eye |
|---|---|---|---|
| 22 | 80 | 4 | SRN, 4 |
| 23 | 77 | 3 | SRN, 3 |
| 24 | 86 | 2 | 2 |
| 25 | 82 | 3 | 3 |
| 26 | 88 | 2 | SRN, 3 |
| 27 | 83 | 2 | 2 |
| 28 | 81 | SRN, 2 | FV scar |
| 29 | | 4 | 4 |
| 30 | | 3 | 3 |
| 31 | | 1 | 1 |
| 32 | | 2 | 2 |

Evaluation of monocyte activity by flow cytometry. Heparinized blood was collected from the 32 ARMD and 10 age-matched control subjects. Phenotypic analysis of peripheral blood monocytes was accomplished by flow cytometry. Plasma levels of macrophage chemo-attractant protein (MCP-1) were determined by Enzyme-linked immunosorbent assay (ELISA).100 microliters of whole blood was stained with anti-CD14-FTIC, anti-CD16-PE (Dako Corporation, Carpenteria, Calif.; FITC=fluorescein isothiocyanate; PE=phycoerythrin), or anti-HLA-DR-PE (Becton Dickinson, San Jose, Calif.) or anti-CCR2-PE. Monocyte activation was also assessed based on a phagocytosis assay (Molecular Probes, Eugene, Oreg.). T-cell evaluation was determined staining with anti-CD4-FITC, anti-CD38-PE, and anti-CD38-PerCP. Negative control antibody (Isotype IgG-FITC, Isotype IgG-PE, (DAKO Corp.), and IgG-Per-CP (Becton Dickinson), was included for each data set. Staining was accomplished by incubation for 20 minutes at room temperature. Red blood cell lysis was accomplished by addition of 2 ml of FACSLYSE (Becton Dickinson), followed by centrifugation at 400×g for five minutes. Supernatants were discarded and cell pellets fixed by addition of 1 ml of fixing solution (1% paraformaldehyde, 0.1% sodium azide, in phosphate-buffered saline, 0.01M, pH7.4). Flow cytometry analysis was performed on a FACSCAN flow cytometer driven by CELLQUEST software (Becton Dickinson). Statistical analysis of selected populations by un-paired t-tests, Newman-Keuls Multiple Comparisons, and Spearman correlations, were performed by GraphPad Prizm software (San Diego, Calif.).

Results

The results of analysis of macrophage activation studies as related to ARMD classification are summarized in Table II.

TABLE II

Immune Parameters of ARMD

| Parameter | All ARMD n = 32 | Dry ARMD n = 9 | Wet ARMD n = 23 | Controls n = 10 |
|---|---|---|---|---|
| HLA-DR | 795 +/ 1276 | 886 +/− 318 | 760 +/− 256 | 662 +/− 261 |
| % CD14/CD16 | 24 +/ 7* | 29 +/8** | 22 +/− 6 | 17 +/− 7 |
| MCP-1 | 466 +/− 295 (n = 12) | 570 +/− 371*** (n = 7) | 320 +/− 91 (n = 5) | 215 +/− 82 (n = 7) |
| % CD4/CD38 | 46 +/− 14 (n = 15) | | | 53 +/− 7 (n = 7) |
| % CD8/CD38 | 37 +/− 11*** (n = 15) | | | 27 +/− 7 (n = 7) |

*p < 0.003 vs controls
**p < 0.011 vs wet
***p < 0.04 vs controls

Figure 2:
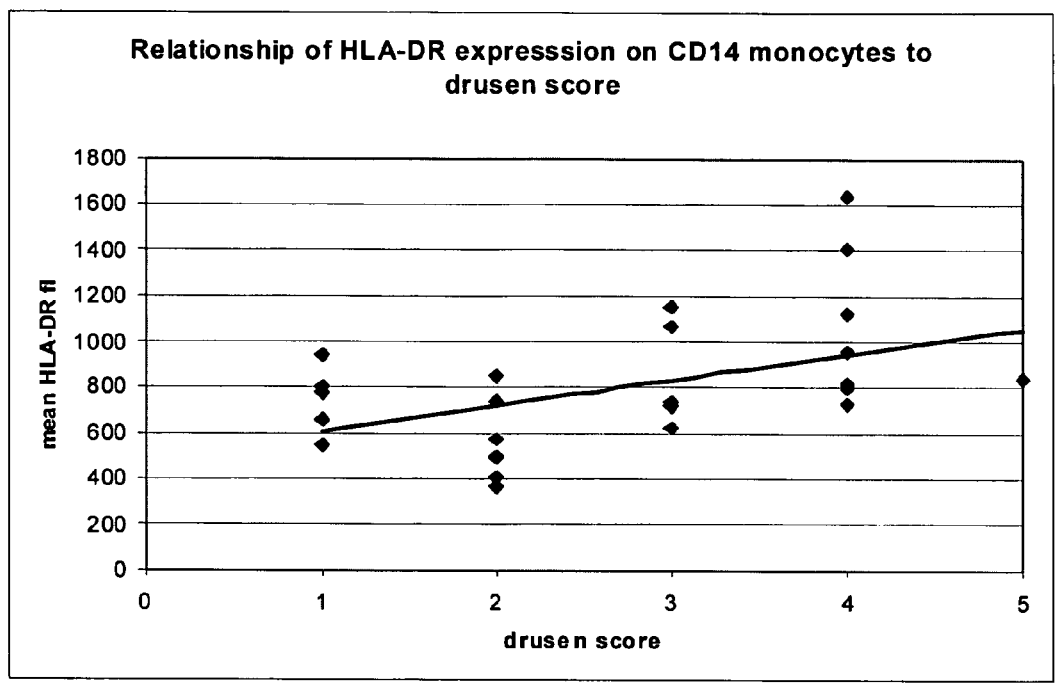
FIG. 2 is a graph showing that higher levels of activated blood monocytes are also associated with higher drusen scores in ARMD patients.

FIG. 1, which is a graph of the relationship between blood macrophage (CD14/16+) and immune activation (CD14/dr level) in ARMD patient samples, shows that the higher the level of macrophages in the blood (% CD14+/16+) the higher the level of activation (higher DR expression/cell) in ARMD patient blood. As shown in FIG. 2, the higher level of blood monocyte activation (as reflected by increasing levels of cell surface HLA-DR concentrations), the higher level of drusen in the eyes of ARMD patients (more severe disease). Therefore, blood macrophage activation is directly correlated to the severity of retinal disease.

Figure 3A:
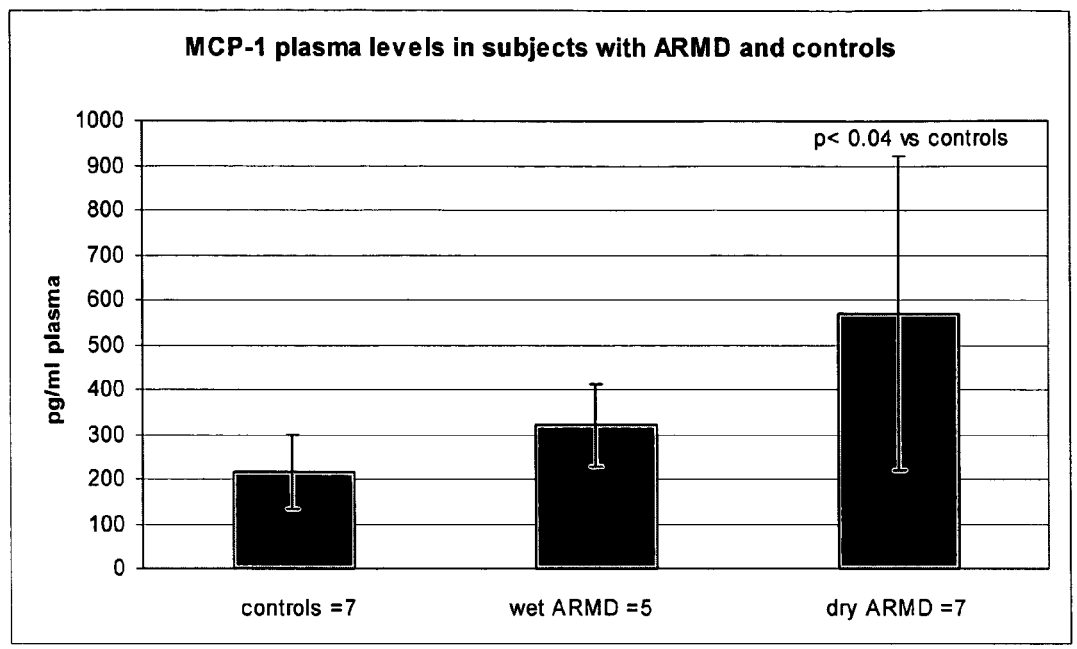
FIG. 3A is a graph showing MCP-1 plasma levels in subjects with wet ARMD (5 patients), dry ARMD (7 patients), and controls.
Figure 3B:
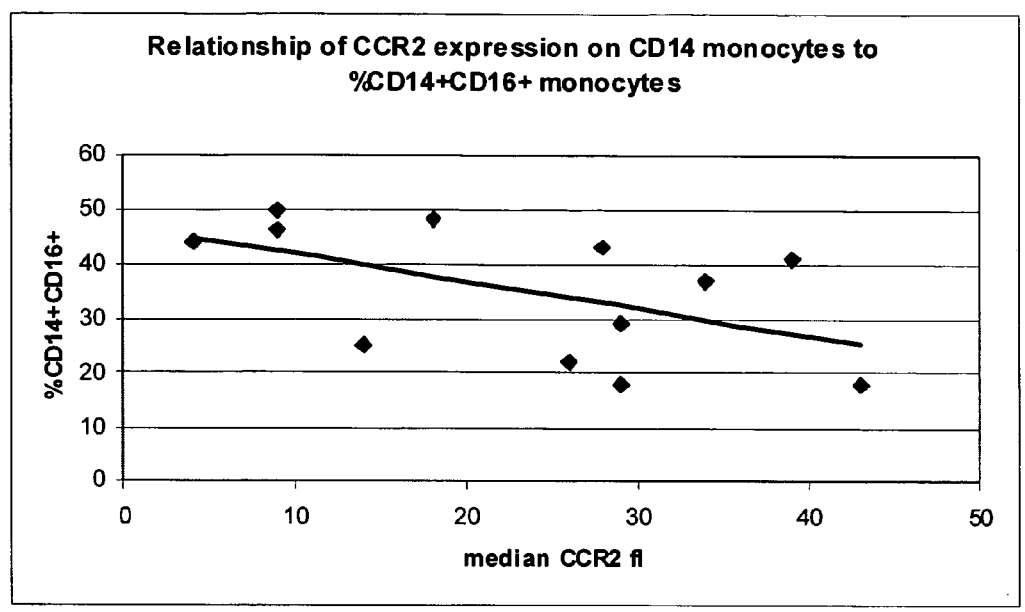
FIG. 3B is a graph showing the relationship between the level of CCR2 expression (which indicates cells are regulated by the MCP-1) and the percentage of peripheral blood monocytes that are CD14+/CD16+ in ARMD patient blood samples. In ARMD patients, the higher the percentage of activated blood macrophages, the lower the level of CCR2 expression.

Plasma levels of MCP-1 were highest for subjects with dry ARMD, compared to controls (p<0.05) (FIG. 3A). The activation marker CD16 was markedly elevated on CD14 monocytes for subjects with dry ARMD compared to subjects with wet ARMD (p<0.01), and compared to normal controls (p<0.001). FIG. 3B shows that activated macrophages (CD14+/CD16+) and expression of the MCP-1 receptor, CCR2, expression are inversely related. That is, the greater the percentage of activated macrophages, the lower the CCR2 expression levels.

Figure 4A:
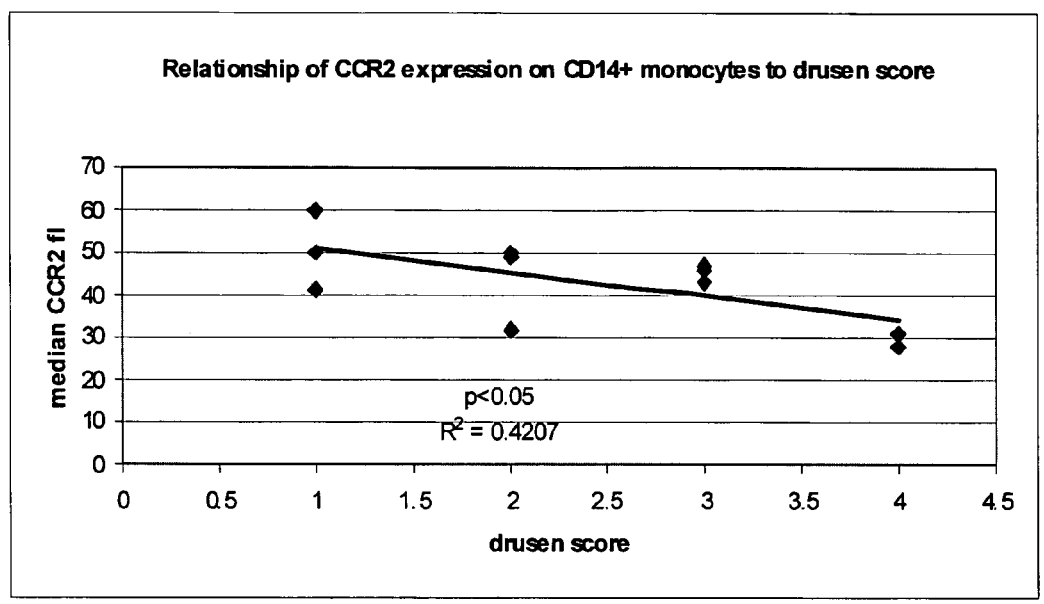
FIG. 4A is a graph showing the relationship between the retinal drusen of ARMD patients and blood monocyte expression of the MCP-1 receptor, CCR2. The data in this figure illustrates that CCR2 expression is is down regulated in direct proportion to the degree of retinal drusen (i.e., CCR2 expression levels and drusen score are inversely correlated, with a decrease in CCR2 expression being associated with an increased drusen score).

FIG. 4A shows the relationship between drusen and blood monocyte expression of the MCP-1 receptor, CCR2. The figures demonstrates that down-regulation of expression of the MCP-1 receptor, CCR2, is directly proportional to the severity of ARMD as measured by drusen score. Further, these data indicate that CCR2 expression and/or MCP-1 levels can be used assess severity of disease, as well as response to therapy.

The results of the experiments show that blood levels of macrophages (CD14+/16+ cells, which include proliferating macrophages (ProMacs)) in ARMD patients parallels the level of cellular activation (level of DR on CD14+ cells). In addition, levels of activated macrophages and ProMacs in the blood parallels levels of drusen in the retina of ARMD patients.

The results also show that there are two parallel markers of disease activity (related to retinal drusen levels) present on macrophages. CD16 and HLA-DR levels on macrophages increases with severity of ARMD. Systemic MCP-1 also increases with severity of disease. In addition, the CCR2 levels of these same macrophages are low relative to non-disease macrophages, indicating down-regulation of the CCR2 receptor by the endogenously produced MCP-1 ligand. These findings indicate that MCP-1 and markers of macrophage activation are indicative of ARMD disease severity, based on their correlation with drusen, the conventional ARMD disease severity marker.

Figure 4B:
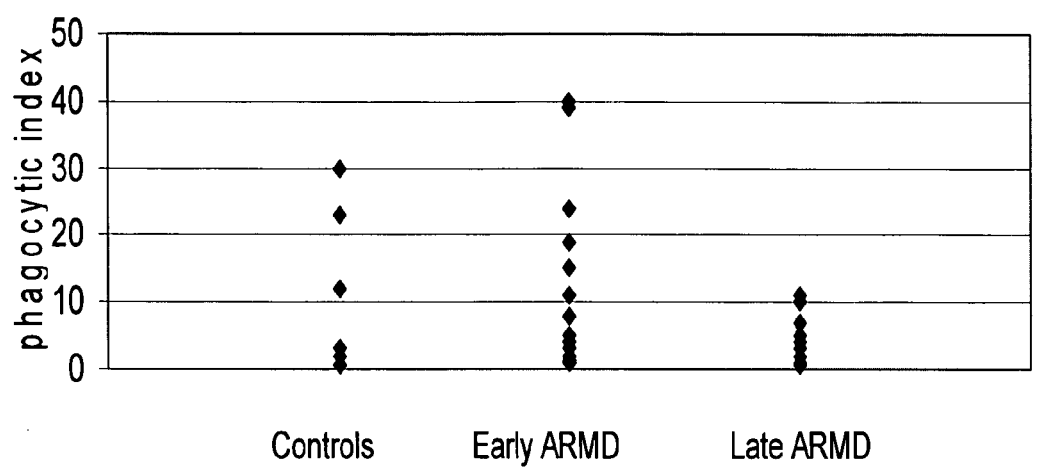
FIG. 4B is a graph showing phagocytic activity of peripheral blood monocytes in control subjects, subjects with early ARMD (drusen score of 1-2), and in subjects with late ARMD (drusen score of 3-4).

The results above indicate that persistently activated macrophages, which includes a population of proliferating macrophages, are elevated in ARMD. Without being held to theory, one possible mechanism for disease involves drusen accumulation in the RPE, which in turn can lead to disease progression. This drusen accumulation may result from reduced ability of macrophages present in the eye to phagocytose, which in turn allows for drusen accumulation To test this hypothesis, CD14+ cells from ARMD patients (early and late ARMD, where early ARMD was defined by a drusen score of 1-2, and late ARMD defined as a drusen score of 3-4) and age-matched controls were assayed for phagocytic ability. FIG. 4B shows that the CD 14+ cells of patients with late ARMD have significantly decreased phagocytic ability, consistent with this model of ARMD progression.

Conclusions: Data presented in this study support a mechanistic model of ARMD that involves systemic immune activation detectable at both the cellular (monocyte and T cell) and cytokine (MCP-1) levels. Abnormal cellular and cytokine activation are correlated with disease severity as assessed by drusen score. These data support a disease model in which systemic immune activation contributes to the evolution of ARMD regardless of "wet" versus "dry" clinical diagnosis. FIG. 4C provides a schematic of this disease model.

Therefore, global therapeutic strategy should focus on the immunological parameters as described herein, rather than the clinical parameters (e.g., drusen accumulation, choroidal neovascularization (CNV), and the like). Systemically activated macrophages in ARMD provide targets for drugs to modulate these immunologic aspects of ARMD pathogenesis. Efficacy of therapies directed toward ARMD can be monitored through analysis of macrophages and MCP-1 levels of blood specimens or other body fluids (e.g., vitreal or aqueous fluid of the eye) or ocular tissue. Examination of parameters of systemic immune response can be performed in conjunction with retinal examination and other conventional parameters of disease. Further, the immune parameters discussed above define immunological differences between the wet and dry forms of disease, and thus useful in disease monitoring and development of effective novel therapies.

Example 2

Effect of Polyamine Analogs on Macrophage Proliferation in ARMD Patients

Percoll gradient separation, which allows for denser cells to be captured, was accomplished as follows. A two-step gradient was prepared in 15 mL conical tubes: bottom layer of 1.087 density Percoll, overlaid with 1.077 density. 1.5 mL whole heparinised blood was mixed with an equal volume of isotonic saline. This blood/saline was layered over the gradient and centrifuged. Cells from the 1.077 and 1.087 interfaces were collected, combined, and washed in 5 volumes of RPMI 1640.

$5 \times 10^5$ PBMCs from ARMD patients (both wet and dry) were isolated through a 1.087 g/cc Percoll/saline gradient as described above, and then were exposed to varied concentrations of polyamine analog after baseline CD14/PCNA staining was performed. The cells were cultured at $5 \times 10^5$ cells in RPMI-1640/10% fetal calf serum in a polypropylene tube (Falcon) at 37° C. for five days. After five days CD14/PCNA staining was performed on control and agent-treated cultures. FACSCAN analysis of PCNA-positive cells in control cultures was compared with agent-treated cultures and the percentage of control PCNA/CD14 cells was calculated. Samples from age-matched normal or Alzheimer's disease (AD) patients were used as controls.

Figure 5:
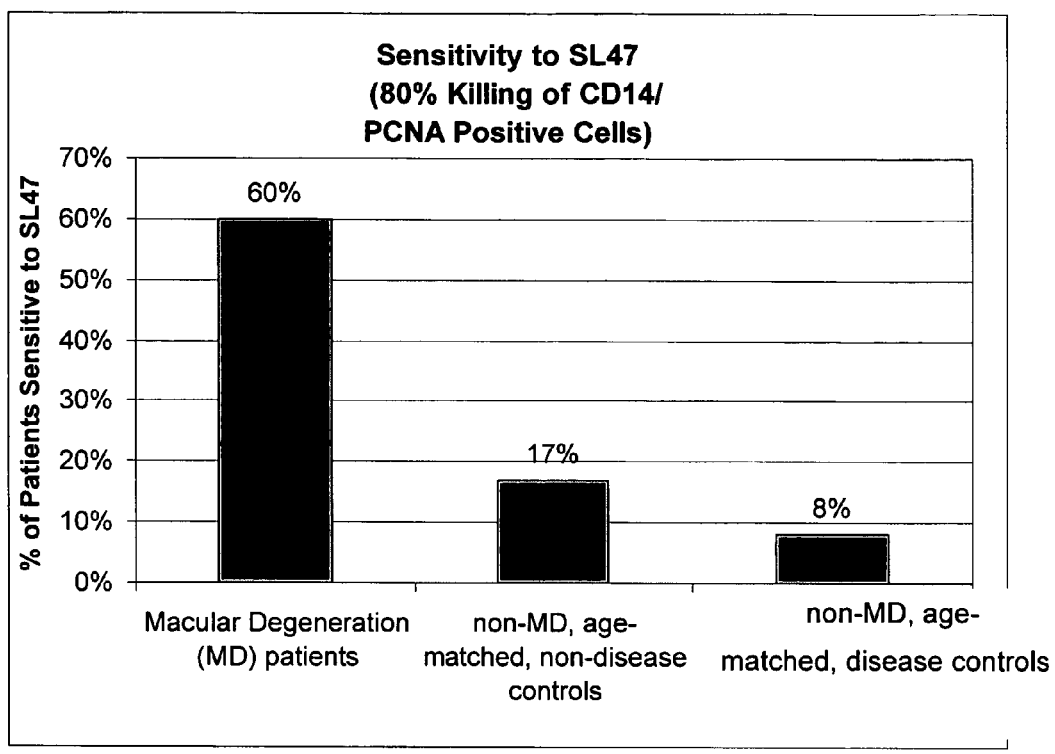
FIG. 5 is a graph showing sensitivity of CD14+/PCNA+ cells to the polyamine analog SL-11047 ("SL47") in ARMD patients ("MD patients"), and age-matched non-ARMD patients (both "non-disease" and "disease" controls).

The results of such an experiment in which the effect of polyamine analog SL-11047 on proliferating macrophages (as detected by PCNA) from the blood of ARMD patients are shown in FIG. 5. This polyamine analog significantly reduced the percentage of proliferating macrophages by at lest 80% in about 60% of ARMD patients. In contrast only 17% of unaffected age-matched subjects had at least 80% killing of CD14/PCNA positive cells. CD14/PCNA cells from age-matched AD patients were similarly killed at only low levels (8% killing). The results of this example shows that polyamine analog SL-11047 kills proliferating macrophages in ARMD. Further, screening of polyamine analogs for activity against proliferating macrophages to identify agents with the most effective killing is warranted.

Figure 6:
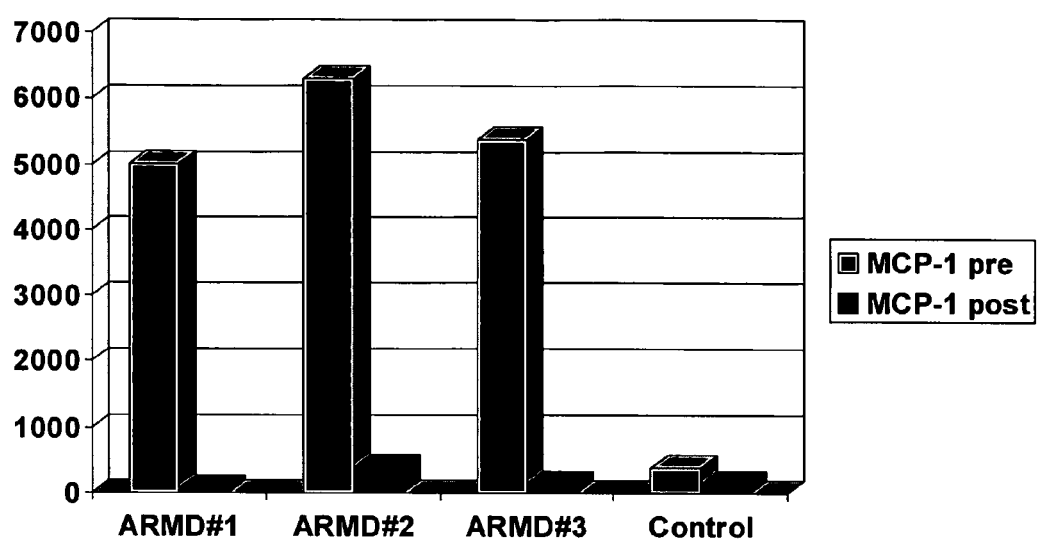
FIG. 6 is a bar graph showing that ARMD blood cells spontaneously produce high levels of MCP-1 ("MCP-1 pre") and that exposure to SL-11047 markedly decreases MCP-1 production ("MCP-1 post").

In culture in which the proliferating macrophages were killed, cell supernatants were evaluated for MCP-1 production. Cells were treated as described above, and MCP-1 collected over a 2 day period that followed a 4 day period of treatment with SL-11047. Cells from an age-matched normal donor were as a control. FIG. 6 shows that ARMID PBMCs spontaneously produce high levels of MCP-1 ("MCP-1 pre"). Exposure of these PBMCs to SL-11047 markedly decreased MCP-1 production (FIG. 6, "MCP-1 post"). These data are consistent with the data in FIG. 6. Thus, killing of CD14/PCNA cells (proliferating macrophages), removes a source of MCP-1, a factor implicated in the pathogenesis of ARMD as discussed above.

Example 3

Polyamine Analog Treatment Improves the Monocyte Phagocytic Index In Vivo

Figure 7:
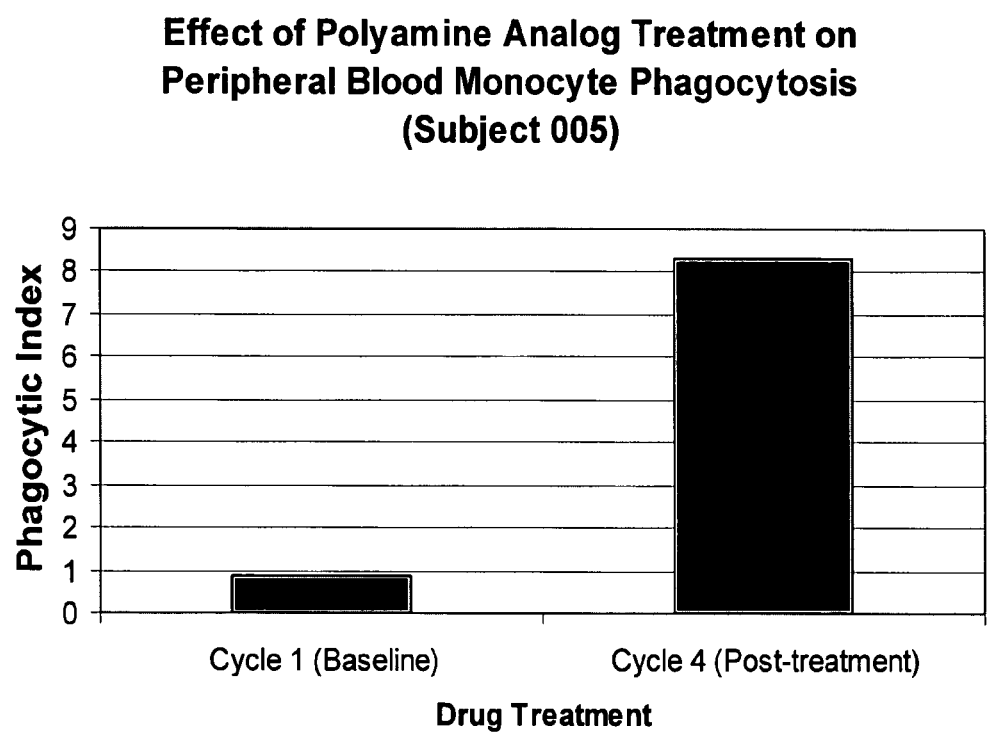
FIG. 7 is a graph showing the effects of polyamine analog treatment on the phagocytic activity of peripheral blood monocytes in a patient prior to and following 4 cycles of polyamine analog therapy.

In order to assess the ability of polyamine analogs to improve phagocytic function, whole blood was obtained from a lymphoma patient pre- and post-administration of SL-11047 (25 mg/m² by infusion per day for 5 days every 3 weeks (one cycle), for a total four cycles) and the phagocytic index assessed as described above. As shown in FIG. 7, abnormal baseline phagocytic function improved significantly after administration of four cycles of SL-11047 polyamine analog therapy. In addition, during the course of therapy, CD16+ cells in the patient decreased to a normal range of the total monocyte population.

Although the foregoing invention has been described in some detail by way of illustration and example for purposes of clarity of understanding it will be apparent to those skilled in the art that certain changes and modifications will be practiced. Therefore, the description and examples should not be construed as limiting the scope of the invention, which is delineated by the appended claims.

What is claimed is:

1. A method of treating, decreasing the symptoms of, or delaying the onset or development of a macrophage-associated ocular disease comprising:
administering to a subject in need thereof an effective amount of a composition comprising MGBG, or a salt thereof.

2. The method of claim 1, wherein administration of the composition causes a decrease in a level of proliferating or activated macrophages in the subject.

3. The method of claim 1, wherein administration of the composition causes an increase in phagocytic activity of proliferating or activated macrophages in the subject.

4. The method of claim 1, wherein administration of the composition causes a decrease in drusen, or inhibits drusen accumulation, in the subject.

5. The method of claim 1, wherein the subject is at risk for a macrophage-associated ocular disease, and wherein administration of the composition causes a delay in the onset or development of the macrophage-associated ocular disease in the subject.

6. The method of claim 1, wherein the macrophage-associated ocular disease is selected from the group consisting of macrophage-associated retinal disease, age-related macular degeneration (ARMD), vitreoretinopathy, and diabetic retinopathy.

7. The method of claim 1, wherein the disease is non-exudative ARMD.

8. The method of claim 1, wherein the composition is associated into a liposome that is optionally conjugated with one or more targeting substance(s).

9. The method of claim 1, wherein the composition further comprises a delivery-facilitating agent, a therapeutic agent, or a combination thereof.

10. The method of claim 1, wherein the composition further comprises a substance selected from the group consisting of zymosan, tetrachlorodecaoxygen (TCDO), MCSF, GMCSF, IL-3, an antibiotic, an anti-inflammatory agent, an anti-angiogenic agent, or a combination thereof.

11. The method of claim 1, wherein the composition is provided as a sustained release formulation.

* * * * *